US009044602B2

(12) United States Patent
Kilby et al.

(10) Patent No.: US 9,044,602 B2
(45) Date of Patent: *Jun. 2, 2015

(54) SEQUENTIAL OPTIMIZATIONS FOR TREATMENT PLANNING

(75) Inventors: Warren D. Kilby, Swinford (GB); Gregory L. Orr, Fremont, CA (US); Etienne Lessard, San Francisco, CA (US); Colin Sims, Chesterfield, MO (US); John R. Dooley, Castro Valley, CA (US); Calvin R. Maurer, Jr., Mountain View, CA (US); Jay B. West, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 468 days.

This patent is subject to a terminal disclaimer.

(21) Appl. No.: 13/446,883

(22) Filed: Apr. 13, 2012

(65) Prior Publication Data
US 2012/0203053 A1    Aug. 9, 2012

Related U.S. Application Data

(63) Continuation of application No. 12/492,793, filed on Jun. 26, 2009, now Pat. No. 8,180,020.

(60) Provisional application No. 61/107,997, filed on Oct. 23, 2008.

(51) Int. Cl.
*A61N 5/10* (2006.01)

(52) U.S. Cl.
CPC ............... *A61N 5/1031* (2013.01); *A61N 5/10* (2013.01); *A61N 5/103* (2013.01); *A61N 5/1042* (2013.01); *A61N 5/1083* (2013.01)

(58) Field of Classification Search
CPC ....... A61N 5/10; A61N 5/103; A61N 5/1031; A61N 5/1042; A61N 5/1083
USPC ........................................... 378/65
See application file for complete search history.

(56) References Cited

U.S. PATENT DOCUMENTS

| 5,398,684 | A | 3/1995 | Hardy |
| 6,038,283 | A | 3/2000 | Carol et al. |
| 6,385,286 | B1 | 5/2002 | Fitchard et al. |
| 6,449,335 | B1 | 9/2002 | Siochi |
| 6,546,073 | B1 | 4/2003 | Lee |
| 6,735,277 | B2 | 5/2004 | McNutt et al. |
| 6,826,254 | B2 | 11/2004 | Mihara et al. |
| 6,853,705 | B2 * | 2/2005 | Chang ............................. 378/65 |
| 6,977,987 | B2 | 12/2005 | Yamashita et al. |
| 7,066,883 | B2 | 6/2006 | Schmidt et al. |
| 7,266,176 | B2 | 9/2007 | Allison et al. |
| 7,362,848 | B2 | 4/2008 | Saracen et al. |

(Continued)

OTHER PUBLICATIONS

International Search Report and Written Opinion of the International Searching Authority, PCT/US2009/055341 filed Aug. 28, 2009, mailed Oct. 14, 2009, 18 pages.

(Continued)

*Primary Examiner* — Allen C. Ho
(74) *Attorney, Agent, or Firm* — Lowenstein Sandler LLP

(57) ABSTRACT

A method and apparatus for radiation treatment planning are described. The method includes receiving a plurality of radiation treatment-planning parameters, and sequentially optimizing the plurality of radiation treatment-planning parameters.

13 Claims, 16 Drawing Sheets

(56) References Cited

U.S. PATENT DOCUMENTS

| | | | |
|---|---|---|---|
| 7,496,173 | B2 | 2/2009 | Goldman et al. |
| 7,529,339 | B2 | 5/2009 | Goldman et al. |
| 7,611,452 | B2 | 11/2009 | Allison et al. |
| 7,734,010 | B2 | 6/2010 | Otto et al. |
| 7,801,270 | B2 | 9/2010 | Nord et al. |
| 7,809,107 | B2 | 10/2010 | Nord et al. |
| 7,817,778 | B2 | 10/2010 | Nord et al. |
| 7,831,018 | B1 * | 11/2010 | Nord et al. ............. 378/65 |
| 8,180,020 | B2 * | 5/2012 | Kilby et al. ............. 378/65 |
| 2003/0208108 | A1 | 11/2003 | Shewmake et al. |
| 2004/0181498 | A1 | 9/2004 | Kothare et al. |
| 2005/0111621 | A1 | 5/2005 | Riker et al. |
| 2007/0078306 | A1 | 4/2007 | Allison et al. |
| 2008/0013687 | A1 | 1/2008 | Maurer, Jr. et al. |
| 2008/0081991 | A1 | 4/2008 | West et al. |
| 2009/0180589 | A1 | 7/2009 | Wang et al. |

OTHER PUBLICATIONS

Jee, K-W. et al. "Lexicographic Ordering: Intuitive Multicriteria Optimization for IMRT," (2007), 1845-1861, 52, Phys. Med. Biol.

Schlaefer, A. et al. "Interactive Multi-Criteria Inverse Planning for Robotic Radiosurgery," in Proceedings of the XVth International Conference on the Use of Computers in Radiation Therapy (ICCR). 2007.

PCT International Search Report and Written Opinion of the International Searching Authority, PCT/US06/36874 filed on Sep. 19, 2006, mailed on Jun. 17, 2008, pp. 8 total.

A. Schlaefer et al., "Stepwise multi-criteria optimization for robotic radiosurgery", Medical Physics, vol. 35, No. 5, May 2008, © 2008 Am. Assoc. Phys. Med., pp. 2094-2103.

Rietzel et al., Four-Dimensional Image-Based Treatment Planning: Target Volume Segmentation and Dose Calculation in the presence of Respiratory Motion, International Journal of Radiation Oncology Biology and Physics, vol. 61, Issue 5, Apr. 1, 2005, pp. 1535-1550.

Paul J. Keall et al., "Four-dimensional radiotherapy planning for DMLC-based respiratory motion tracking", Med. Phys. 32 (4), Apr. 2005, pp. 942-951.

Paul Keall, "4-Dimensional Computed Tomography Imaging and Treatment Planning", Seminars in Radiation Oncology, vol. 14, No. 1, Jan. 2004: pp. 81-90.

Popple, R.A. et al. (Nov. 2005). "Simultaneous Optimization of Sequential IMRT Plans," Medical Physics 32 (11):3257-3266.

Woudstra, E. et a. (2008). "A Comparison of an Algorithm for Automated Sequential Beam Orientation Selection (Cycle) with Simulated Annealing," Physics in Medicine and Biology 53:2003-2018.

European Search Report for Europe Application No. 09822371.2, mailed Jun. 26, 2012, 5 pages.

* cited by examiner

| VOI Limits | | | | | | | |
|---|---|---|---|---|---|---|---|
| VOI Name 564 | Use 562 | Max Dose (cGy) 552 | Boundary Only 566 | Importance Sampling 560 | Voxels per Beam 558 | Skip Factor 556 | #Constraints 554 |
| prostate | ☐ | 0.00 | | | | | |
| urethra | ☑ | 4180.00 | | | 1 | 4 | 345 |
| PTV | ☑ | 780.00 | | | 1 | 2 | 2586 |
| bladder | ☑ | 4180.00 | ☑ | | 1 | 1 | 3153 |
| rectum | ☑ | 3380.00 | | | 1 | 1 | 3205 |
| Bulb | ☐ | | | | | | |
| PTV - Shell 1 | ☑ | 3800.00 | ☑ | | 1 | 1 | 1624 |
| PTV - Shell 2 | ☑ | 1800.00 | | | 1 | 2 | 1859 |

[Update] [OK] [Cancel]

| Type 801 | Objective 802 | Description 803 | DVH 804 808 |
|---|---|---|---|
| Target | Optimize Minimum Dose (OMI) | Maximizes and then constrains the minimum dose delivered to the target. Set the goal to the desired minimum dose level to be achieved everywhere within the target. | 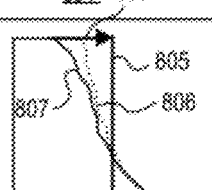 |
| | Optimize Coverage (OCO) | Maximizes and then constrains the voxels that receive as close as possible to a specified dose. Set the goal to the dose level for the desired volume to be maximized (e.g. a prescription dose) | 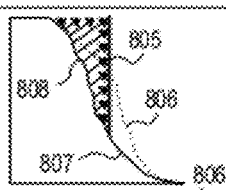 |
| | Optimize Homogeneity (OHI) | Maximizes and then constrains the voxels that receive as close as possible to the maximal dose. The goal is automatically set to the maximal dose constraint, and therefore the action is to maximize dose homogeneity | 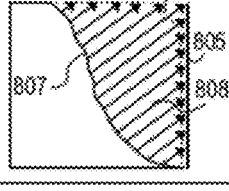 |
| Critical structure | Optimize Maximum Dose (OMA) | Minimizes and then constrains the maximum dose delivered to the critical structure. Set the goal to the desired maximum dose to be achieved everywhere within this critical structure. | 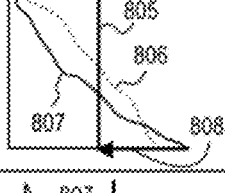 |
| | Optimize Mean Dose (OME) | Minimizes and then constrains the voxels that receive as close to the specified dose value as possible. Set the goal to the dose level for the desired volume to be minimized. | 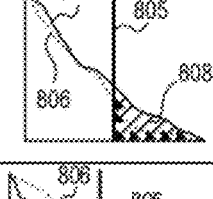 |
| Auto-shell structure | Optimize Conformality (OCI) | Minimizes and then constrains the maximum dose delivered to the auto-shell structure. Set the goal to the maximum dose to be achieved everywhere along the auto-shell structure. | 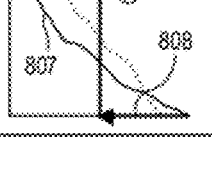 |

FIG. 8

SEQUENTIAL OPTIMIZATIONS FOR TREATMENT PLANNING

RELATED APPLICATIONS

This application is a continuation of U.S. patent application Ser. No. 12/492,793, filed Jun. 26, 2009, now U.S. Pat. No. 8,180,020, issued on May 15, 2012, which claims the benefit of U.S. Provisional Application No. 61/107,997, filed Oct. 23, 2008, which are hereby incorporated by reference in its entirety.

TECHNICAL FIELD

Embodiments of the present invention relate generally to radiation treatment planning and, more particularly, to sequentially optimizing a radiation treatment plan.

BACKGROUND

Conventional radiosurgery systems use forward treatment planning or inverse treatment planning to treat pathological anatomies (e.g., tumor, lesion, vascular malformation, nerve disorder, etc.) during radiation treatment (e.g., radiosurgery or radiotherapy). In forward treatment planning, a medical physicist determines how the radiation source (beams) will be configured to apply the desired radiation dose to a tumor and then calculates how much radiation will be absorbed by critical structures (i.e., vital organs) and other healthy tissue. In inverse treatment planning, in contrast to forward planning, the medical physicist specifies the minimum and maximum doses to the tumor and the maximum dose to other healthy tissues independently, and the treatment planning system then selects the direction, size, total number, and sometimes energy of the radiation source's beams in order to achieve the specified dose conditions. Conventional treatment planning systems are designed to import 3-D images from a diagnostic imaging source, for example, computerized x-ray tomography (CT) scans. CT scans provide an accurate three-dimensional model of a volume of interest (e.g., skull or other tumor-bearing portion of the body) generated from a collection of CT slices and, thereby, the volume requiring treatment can be visualized in three dimensions. The VOIs are usually represented as voxels (volume elements), similar to pixels in a 2-D image.

During inverse planning, once the software package has imported the CT scans, the medical physicist manually delineates the extent of a volume of interest (VOI) in the CT to delineate a structure to be targeted or avoided with respect to the administered radiation dose. That is, the radiation source's beams are positioned in a sequence calculated to localize the radiation dose into a VOI that conforms as closely as possible to the target requiring treatment, while avoiding exposure of nearby healthy tissue. Once the target (e.g., tumor) VOI has been defined, and the critical and soft tissue volumes have been specified, the responsible radiation oncologist or medical physicist specifies the minimum and maximum radiation doses to the target VOI, and the maximum dose to normal and critical healthy tissue. The software then produces an inverse treatment plan, relying on the positional capabilities of the radiation treatment system, to meet, as closely as possible, the min/max dose constraints of the treatment plan.

FIG. 1 is a conceptual illustration of a graphical output of a treatment planning system displaying a slice of a CT image. The illustration of the CT image includes a pathological anatomy that is targeted for treatment, as well as a critical region that is located near the pathological anatomy. Conventionally, a user manually delineates points (e.g., some of the dots on the contour lines of FIG. 1) on the display that is used by the treatment planning system to generate a contour around the critical region and a target region contour around the pathological anatomy. Based on specified minimum and maximum doses to the target region and the maximum dose to the critical region, the treatment planning system generates a dose isocontour for the target region (e.g., lines joining points of equal dose, expressed in absolute units, for example, 40 Gy, 50 Gy, etc., or as a percentage of a maximal or user defined dose, for example, 60%, 70%, 80%, etc.). Ideally, the isocontour of the desired dose to be delivered to the target should perfectly match the contour of the target region. In some cases, the dose isocontour generated by the treatment planning system is not optimal, and can include portions of the critical region, as illustrated in FIG. 1.

Two principal requirements for an effective radiation treatment system are dose conformality, and to a lesser extent, homogeneity. Homogeneity is the uniformity of the radiation dose over the volume of the target (e.g., pathological anatomy such as a tumor, lesion, vascular malformation, etc.) and can be characterized by a dose volume histogram (DVH). An ideal DVH for the pathological anatomy is often considered a rectangular function as illustrated in FIG. 2, where the dose is 100 percent of the prescribed dose over the entire volume of the pathological anatomy. A desirable DVH for a critical region would have the profile illustrated in FIG. 3, where the volume of the critical anatomical structures receives as little of the prescribed dose as possible.

Conformality is the degree to which the desired dose isocontour of the radiation dose distribution matches (conforms) to the shape and extent of the target (e.g., tumor) in order to minimize damage to critical adjacent structures. More specifically, conformality is a measure of the amount of prescription (Rx) dose (amount of dose applied) within a target VOI. Conformality may be measured using a conformality index (CI)=(total volume at >=Rx dose)/(target volume at >=Rx dose). Perfect conformality results in a CI=1.

The treatment planning process typically requires a user to employ a treatment planning software program to complete many treatment-planning objectives like target coverage, conformality and homogeneity of the dose distribution, treatment time, etc. In order to optimize the treatment plan, conventional treatment planning software programs group multiple treatment-planning objectives into a single mathematical cost function and optimize the entire cost function. By optimizing the single cost function, the treatment planning software program optimizes the multiple treatment-planning objectives together, simultaneously and collectively.

In one conventional approach to prioritizing one treatment-planning objective over another, a user specifies a weighting factor for each of the treatment-planning objectives. Yet, because the objectives are optimized simultaneously and collectively, there is limited control of the resulting trade-off between the multiple treatment-planning objectives. In addition, because the objectives are optimized simultaneously and collectively, the user may have to run this collective optimization process many times, assessing the treatment plan after each optimization iteration, and manually modifying parameters, such as the weighting factor or a dose constraint, in an attempt to improve the optimization. This manual and iterative optimization process requires time and user experience in changing the treatment-planning parameters to improve the optimization process. In addition, because treatment plans differ from patient to patient, as well as from treatment region to treatment region (e.g., cranial versus lung), the treatment planning system requires the user to manually input parameters throughout the treatment planning process for each different treatment plan. This manual process requires time, can result in less than optimal treatment plans, and has the potential to result in user-input errors.

BRIEF DESCRIPTION OF THE DRAWINGS

The present invention is illustrated by way of example, and not by way of limitation, in the figures of the accompanying drawings.

FIG. 5B illustrates one embodiment of a user interface that allows a user to define the maximum doses and the sampling parameters for each VOI in the optimization.

FIG. 5C illustrates one embodiment of a user interface that allows a user to define the target volume for which a shell structure is desired, and the symmetric or asymmetric dilation margins.

FIG. 6 illustrates one embodiment of a user interface that allows a user to define an ordered sequence of optimization steps.

FIG. 8 is a table of exemplary optimization steps according to one embodiment.

DETAILED DESCRIPTION

Figure 1:
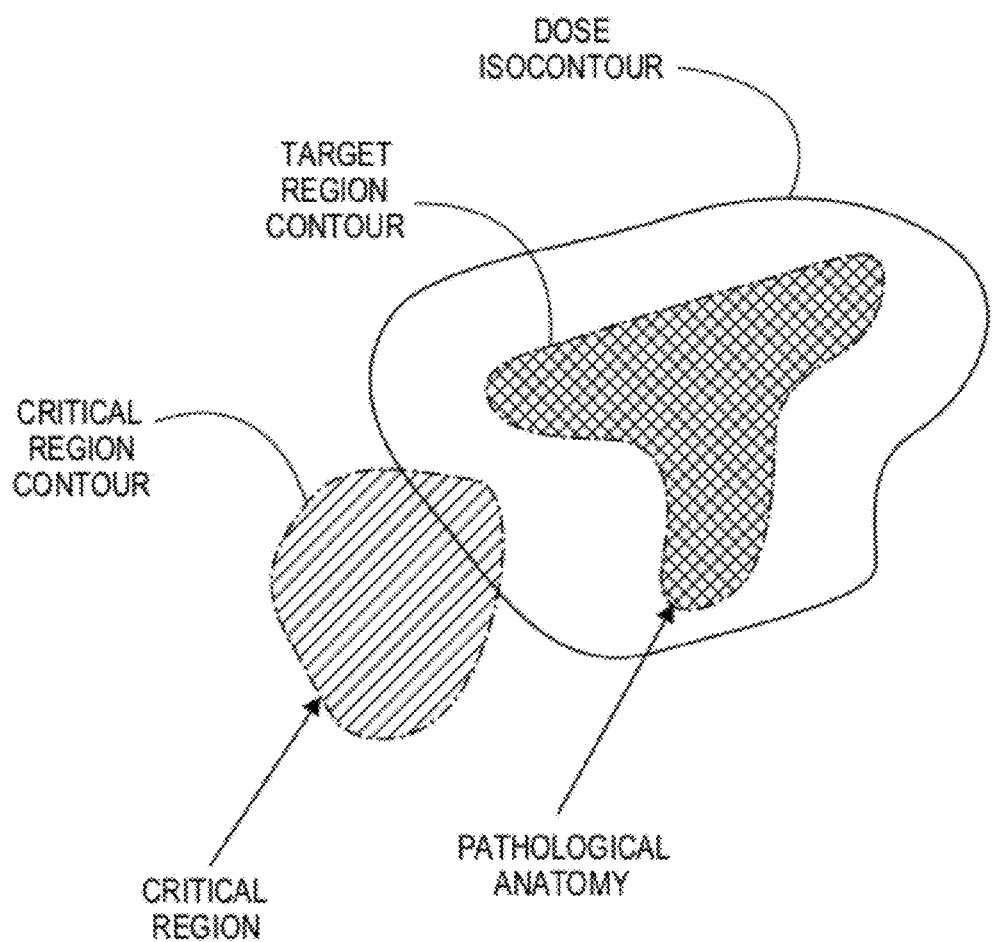
FIG. 1 illustrates a graphical output of a treatment planning system displaying a slice of a CT image.
Figure 2:
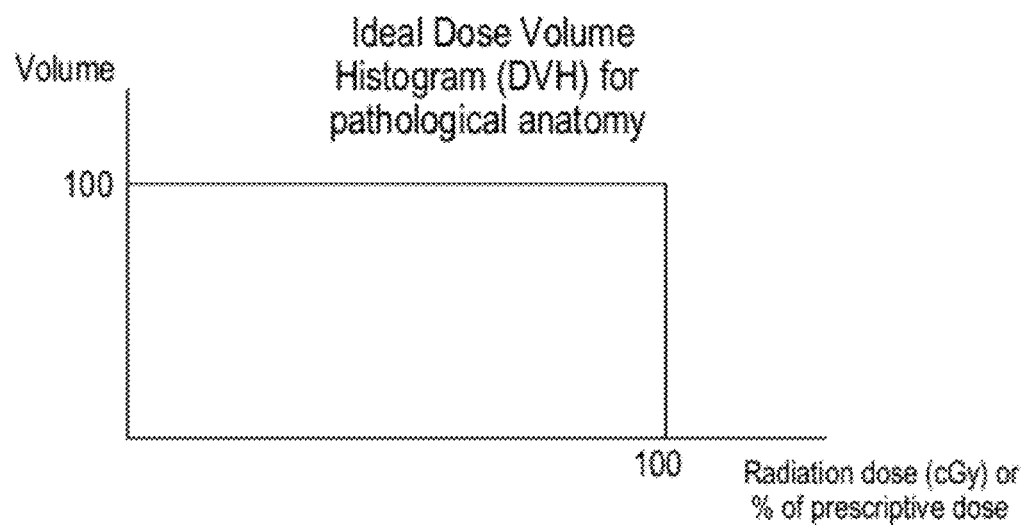
FIG. 2 is an ideal DVH for a pathological anatomy.
Figure 3:
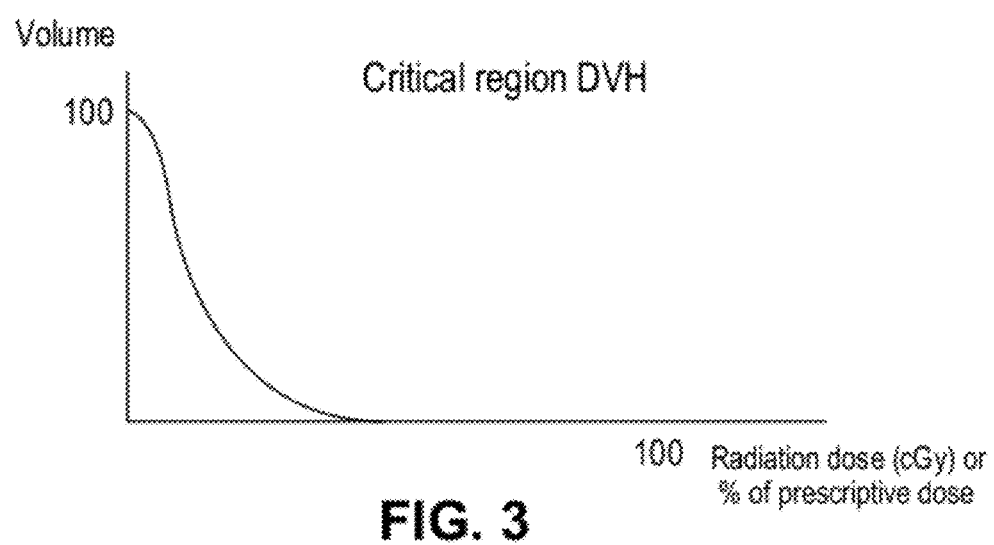
FIG. 3 is a desirable DVH for a critical region.
Figure 4A:
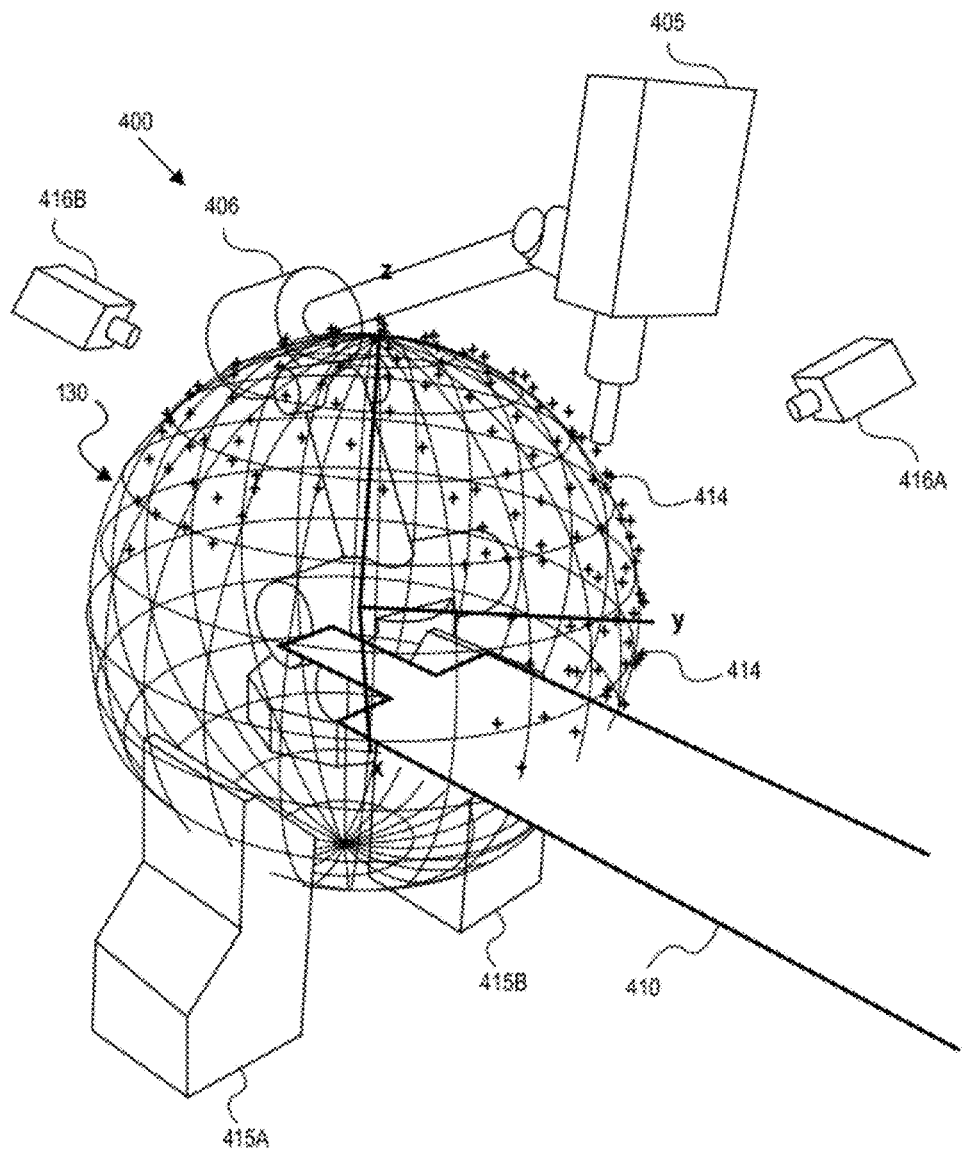
FIG. 4A is a block diagram of one embodiment of a radiation treatment delivery system.

FIG. 4A illustrates a radiation treatment delivery system 400, which includes a linear accelerator (LINAC) 405 (radiation source) mounted on a robotic arm 406, a treatment couch 410 mounted on a second robotic arm (not illustrated), image detectors 415A and 415B, and imaging sources 416A and 416B. Accuray Incorporated of Sunnyvale, Calif. makes and sells a system such as that illustrated in FIG. 4A. Preferably, radiation treatment delivery system 400 is used to perform radiation treatment (e.g., radiosurgery and/or radiotherapy), i.e., the treatment or destruction of a lesion (e.g., tumor) within a patient.

Preferably imaging sources 416 and detectors 415 act as an imaging guidance system, as a skilled artisan will appreciate, to provide control over the position of treatment couch 410 (with the patient thereon) and the targeting of radiation beams from the LINAC 405 towards the target VOI within the patient. Preferably, robotic arm 406 has multiple (e.g., six) degrees of freedom capable of positioning LINAC 405 with an almost infinite number of possibilities within its operating envelope, depicted as an approximate sphere around the patient. To resolve various treatment planning and collision problems, preferably the robotic arm 406 positions LINAC 405 to a finite number of spatial nodes from which the LINAC 405 may emit a radiation beam towards the target VOI and to create specific paths (known safe paths) that robot arm 406 must follow between the spatial nodes to avoid collisions. A collection of spatial nodes and associated safe paths interconnecting these spatial nodes is called a "workspace" or "node set". FIG. 4A illustrates an approximate spherical workspace 130, including a number of spatial nodes 414 each represented by a "+" symbol (only a couple are labeled). The skilled artisan will appreciate that any number shapes of workspaces may be used. Although a system having a LINAC mounted on a robotic arm is used in the present description, the skilled artisan will appreciate that the invention disclosed herein applies to other types of radiation surgery and radiation therapy devices, for example and without limitation to a gantry mounted LINAC, such as that manufactured and sold by Varian Medical Systems.

In order to utilize a radiation treatment delivery system, such as that just described, the system requires a treatment plan for the delivery of radiation to the target VOI. The present invention is directed to a method and a treatment planning system for sequentially optimizing radiation treatment-planning parameters in the generation of a radiation treatment plan. A radiation treatment-planning parameter is an attribute of a radiation treatment plan, as described below. Parameters, for the purpose of this description, are divided into two categories, non-optimizable parameters (e.g., CT images, node positions, target, critical structures or shell structures), and optimizable parameters (e.g., mean dose to a critical structure, homogeneity, or maximum dose to a critical structure). In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

In contrast to the conventional optimization process described above, in which multiple treatment-planning objectives are grouped together and optimized in a single cost function, the embodiments described herein sequentially optimize multiple treatment-planning objectives as an ordered sequence of individual optimization steps. For the purpose of the present description a treatment planning objective comprises three things: (i) an optimizable parameter (described more fully below); (ii) an optimization instruction (direction of optimization); and (iii) a goal value (described more fully below). In one embodiment, each treatment-planning objective is optimized by means of a linear programming algorithm applied to a single optimizable parameter. The optimization process comprises optimizing each of the treatment planning objectives in the ordered sequence, while obeying constraints related to values of other planning parameters (these constraints may be applied for the entire optimization process, or may be related to values of other parameters achieved through previous optimization steps). The linear programming optimization includes, for example and without limitation, a Simplex algorithm to perform the sequential optimization, or, as will be recognized by the skilled artisan, a variety of algorithms may be used to perform the sequential optimization. For example, additional optimization objectives or steps, which may not be efficiently optimized with linear programming algorithms, may use other types of optimization algorithms.

Examples of treatment-planning objectives include, without limitation, maximizing target volume coverage by a defined dose level, maximizing the minimum dose within a target volume, attempting to reduce maximum or mean dose delivered to critical structures (e.g., healthy tissue, organs, bone structures, etc) to a goal value, attempting to reduce total MUs delivered to a goal value, attempting to increase target volume dose homogeneity to a goal value, and attempting to increase conformality of the dose distribution around the target volume to a goal value. Each of these treatment-planning objectives has an associated optimizable planning parameter (e.g. maximum dose to the bladder), an optimization direction (e.g., minimize) and a goal value (e.g., 5 Gy). Alternatively, other types of treatment-planning objectives may be accomplished using sequential optimization steps. In this manner, each optimizable parameter is optimized separately and in sequence.

The ordered sequence of optimization steps, also referred to herein as a script, may be defined by the user to prioritize the treatment-planning objectives, instead of manually defining weighting factors for each objective in the conventional single cost function approach. Using certain embodiments described herein, the user's clinical knowledge may be applied more directly to the treatment-planning problem, for example, by sequentially optimizing the treatment-planning objectives in a prioritized order established by the user. Alternatively, the user may utilize a previously saved script already having the desired sequenced order for a particular treatment, e.g., script for treating prostate, which may also include any or all of the treatment-planning objectives and constraints. In such an embodiment, the user may be given the ability to modify the objectives and constraints in order to customize the script for a particular patient.

In one embodiment, a treatment planning system (TPS), during sequential optimization, applies the result of each optimization step (e.g., optimized parameter) as an additional constraint to the next optimization step as further explained below. In this manner, the treatment-planning parameter optimized at each step cannot degrade as a result of subsequent optimization steps; although, embodiments of the present invention do permit subsequent optimization steps to change a previously optimized treatment-planning parameter by at most a pre-set amount (a relaxation value, described below).

Also, in contrast to the conventional optimization process described above, in which the user manually enters parameters throughout the treatment planning process for each different treatment plan, embodiments of the present invention retrieve the script from memory, with the ability to automatically generate an optimized treatment plan by executing the script. The user may have the ability to modify the parameters of the script to customize it for a particular patient. A script is an ordered sequence of optimization steps or objectives, or a data structure including one or more parameters that can be stored, loaded, edited, and/or retrieved, and executed/optimized in the ordered sequence by the TPS. The script may also contain other non-optimizable parameters and/or other user-inputs, such as absolute constraints that must be respected during each step of the sequential optimization process as described below. In one embodiment, the TPS imports the stored script and automatically executes the script resulting in an optimized treatment plan. In another embodiment, the TPS imports the stored script, and allows a user to review and edit the stored script, if desired. The modified script may also be stored in memory with the TPS, or in an external storage device, as would be appreciated by one of ordinary skill in the art.

As described, the TPS may also contain pre-created scripts that can be accessed by a user. For example, a user may load non-optimizable parameters (e.g., CT image(s), contour VOIs in the CT image(s)) and load a stored script for execution and sequential optimization to produce an optimized treatment plan with minimal user input. The stored scripts may be automatically executed, or may be modified by the user before execution. Whether or not modifications are made to the stored script, developing a treatment plan using the stored script takes less time than the conventional approaches, and will be less susceptible to user-input error. For example, the stored scripts may serve as examples for a less experienced user, or as templates for users of any experience level. In one embodiment, the stored script can be used in conjunction with templates of a workflow management system, such as the wizard-like workflow management system described in a commonly owned patent application, U.S. Pat. No. 7,611,452, filed Sep. 30, 2005, which is incorporated herein in its entirety for all purposes. The templates may provide one or more pre-defined parameters and settings applicable to the anatomical treatment region of interest (e.g., parameters and settings based on past treatments that were successful for a particular body region); whereas, the stored scripts provide an ordered sequence of optimization steps or objectives that can be executed to provide an optimized treatment plan using the pre-defined parameters and settings from a template. In one embodiment, one or more scripts are stored as part of one or more templates of the TPS. Upon user selection of a particular template for a particular region of interest, the TPS can automatically load the pre-defined treatment planning parameters and settings for the region, as well as the corresponding script. The TPS can automatically execute the script to develop an optimized treatment plan, or allow the user to manually modify the script and/or pre-defined treatment planning parameters to customize the script for a particular patient. The use of a wizard user interface and templates, including the stored script, may provide the advantage of reducing the time required to complete the treatment planning process, reducing user error, and may also provide a method to simplify the various tasks involved in the treatment planning workflow, as described in the commonly owned patent application.

FIGS. 4B-7B and the corresponding description provide an example of optimizing a treatment plan for a prostate tumor case using an image-guided, robotic radiation treatment system, such as that described above, of which the CYBERKNIFE® system, developed by Accuray Incorporated of California, is an example. As will be appreciated by one of ordinary skill in the art, the embodiments described herein may be used to optimize treatment plans for other target structures/lesions, and may use other types of radiation treatment systems, for example, a gantry based (isocentric) intensity modulated radiotherapy (IMRT) system.

In developing an optimized radiation treatment plan for a prostate tumor, the TPS can import one or more 3-D images from a diagnostic imaging system, and optionally fuse two or more images from different imaging modalities with one another, to allow three dimensional visualization of the volume requiring treatment. The TPS can be used to generate contours for one or more VOIs to be targeted or avoided during treatment, such as a planning target volume (PTV), the prostate, bladder, rectum, penile bulb, and PTV shell structures. Shell structures may be used as part of the treatment plan to influence dose distribution. For example, but without limitation, shell structures can be automatically generated around the target volumes based on symmetric or asymmetric dilations of the target volume. Shell structures are tuning structures generated to restrain the dose delivered to the normal tissues surrounding the target volume, and together with maximum dose constraints may be used to control the conformality of the dose distribution around the target volume. For example, maximum dose constraints applied to a shell structure generated in the close vicinity of the target volume (e.g., dilation margins of 1 to 5 mm) would control the conformality of the prescription isodose, and maximum dose constraints applied to a shell structure generated further away from the target volume (e.g., dilation margins of 10 to 30 mm or greater) would control the low dose extensions around the target volume. The shell structure's target volume and dilation margins may be saved as components of the sequential optimization script. In one embodiment, when a script that includes shell structures is loaded, the shell structures are automatically generated. Alternatively, the shell structures can be manually generated. After a user or the TPS generates the contours of the one or more VOIs, the TPS performs inverse planning to optimize the radiation treatment plan, as described in the embodiments below.

A radiation treatment plan comprises many different attributes, including without limitation: a set of radiation beams to be directed at an anatomical region (e.g., prostate region of a patient); beam parameters for each of the radiation beams, such as, for example, a beam position (e.g., node), a beam orientation, a beam intensity, a beam duration or equivalently a number of monitor units (MU), a field size; non-optimizable parameters, such as VOIs, CT images, etc; and optimizable parameters, such as homogeneity, conformality, maximum doses to critical structures, etc.

Radiation treatment-planning parameters are data that represent characteristics of physical and tangible objects, for example and without limitation the radiation applied to an anatomical region of the patient via radiation beams. Some treatment planning parameters are optimizable: for example, one optimizable parameter is the total number of MUs for all radiation beams, and another optimizable parameter is the maximum or minimum dose of radiation received by a volume of interest (e.g., prostate, rectum, or bladder) within the anatomical region of the patient to which the radiation beams are directed. When acted upon by the TPS, the raw data is transformed into values for the beam parameters of the radiation beams, the radiation beams being tangible and physical objects, which are directed at the anatomical region of the patient. For example, the TPS transforms the raw data into quantities for a number of radiation beams, a beam position, a beam orientation, a beam intensity, a beam duration, and a field size for each radiation beam. These transformed values represent a configuration of a set of one or more radiation beams (referred to herein as the optimized treatment plan), which is directed at the anatomical region of the patient for radiation treatment.

Figure 4B:
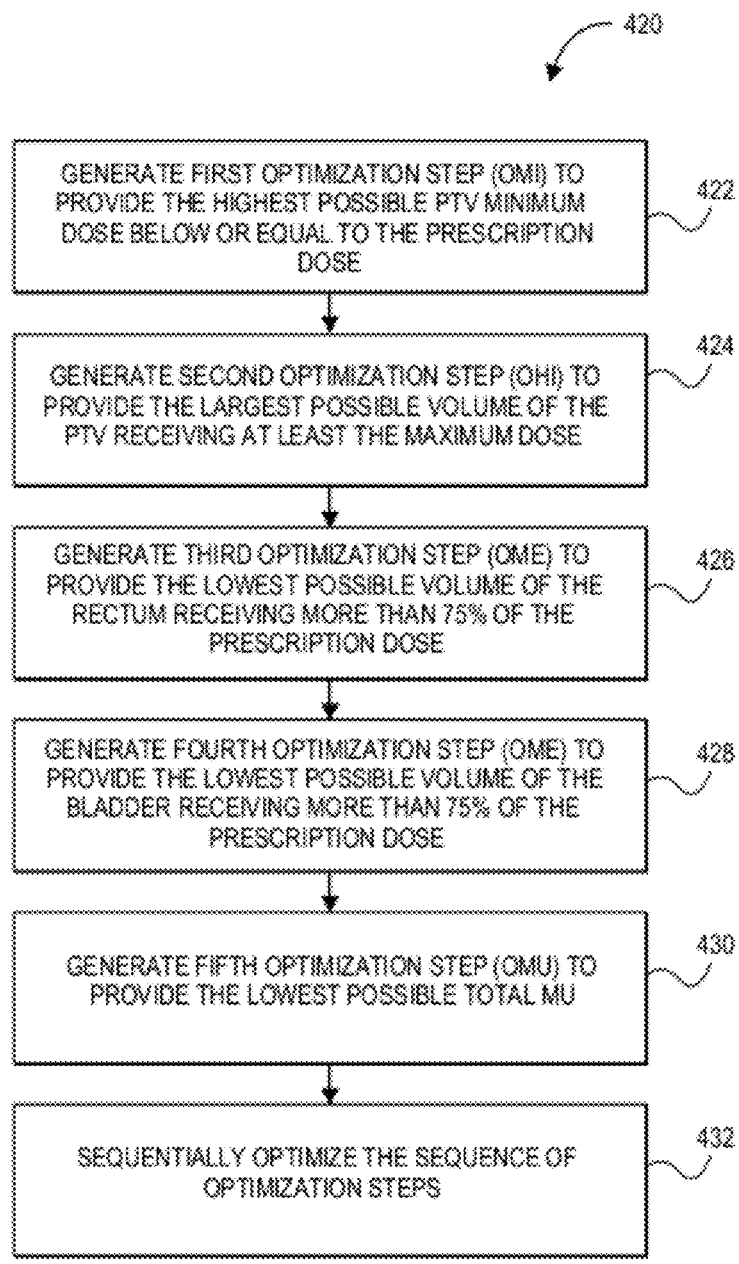
FIG. 4B is a flow diagram of one exemplary embodiment of a method of generating a script for treating a prostate tumor.

FIG. 4B is a flow diagram of one exemplary embodiment of a method 420 of generating a script for treating a prostate tumor. The method 420 is performed by processing logic that may comprise hardware (circuitry, dedicated logic, etc.), software (such as is run on a general purpose computer system or a dedicated machine), firmware (such as embedded software), or any combination thereof. For convenience and not limitation, the processing logic has been referred to below as the TPS. In one embodiment, the method 420 is performed by a processing device (e.g., processing device 3010 of FIG. 11) of a treatment planning system.

Typically, in prostate cases, the primary treatment-planning objectives are to optimize dose homogeneity of the PTV (e.g., target volume associated with the prostate) and optimize the minimum dose to the surrounding critical structures. It should be noted that the treatment-planning objectives may include more or less optimization steps as described herein; for example, in the prostate case, there may be a need to minimize mean dose or dose to limited sub-volumes as would be appreciated by one of ordinary skill in the art having the benefit of this disclosure. Each of the treatment-planning objectives can be achieved by sequentially optimizing treatment-planning parameters (e.g., maximum or minimum doses to the target and critical structures) using a sequence of optimization steps. In each optimization step, the user either establishes an acceptable optimized value for that treatment-planning parameter, i.e., a goal value (discussed further below), or may leave the value blank indicating the TPS should attempt to achieve an optimum value (further discussed below) for that treatment-planning parameter. In order to prioritize the treatment-planning objectives, the TPS generates the script, based on user-input in this embodiment, where each optimization step may correspond to a treatment-planning objective. In response to user-input, the TPS generates (blocks 422-430) and executes (block 432), in a user-defined or TPS-generated preferred sequential order, a series of optimization steps to achieve the treatment planning objectives: a first optimization step (optimize minimum dose (OMI), block 422) to deliver to the PTV the highest possible minimum dose below or equal to a first goal value (e.g., 38 Gy); a second optimization step (optimize homogeneity (OHI), block 424) to deliver to the PTV the highest possible mean dose below or equal to a second goal value, therefore maximizing homogeneity; a third optimization step (optimize mean dose (OME), block 426) to attempt to reduce the mean dose to the rectum to a third goal value; a fourth optimization step (optimize max dose (OME), block 428) to attempt to reduce the mean dose to the bladder to a fourth goal value; and a fifth optimization step (optimize monitor units (OMU), block 430) to minimize the total number of MU delivered. In another embodiment, another optimization step may attempt to reduce the mean or maximum dose to the urethra to a specified goal value. Once the optimization steps of the script have been generated, the TPS executes each of the optimization steps of the script individually and in sequence (block 432) to generate an optimized treatment plan. It will be appreciated that treatment-planning parameters for use during the optimization steps may be provided by the user, obtained from memory or both, and that the TPS may optimize more or fewer treatment-planning parameters as illustrated and described with respect to this embodiment, such as illustrated in method 450 of sequential optimization of FIG. 4C.

Figure 4D:
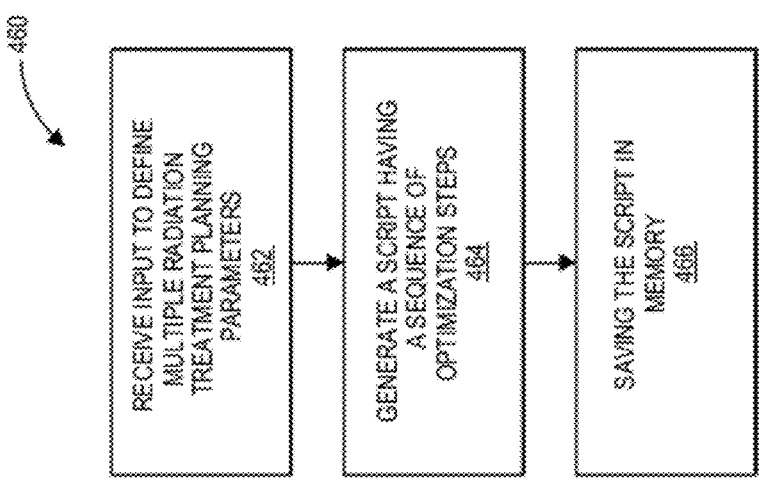
FIG. 4D is a flow diagram of another embodiment of a method of generating a script having an ordered sequence of individual optimization steps.
Figure 4C:
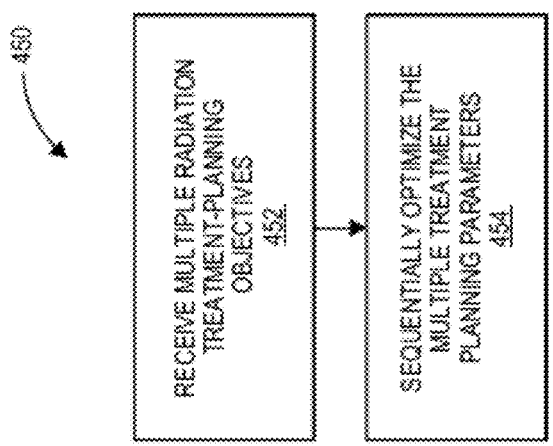
FIG. 4C is a flow diagram of one embodiment of a method of sequential optimization of multiple radiation treatment-planning parameters.

FIG. 4C illustrates another embodiment of the how the TPS optimizes a treatment plan. The TPS begins with receiving multiple radiation treatment-planning objectives of a treatment plan (block 452) from memory or from the user (for example: values for the desired minimum dose to the target volume, mean dose to a critical structure (e.g. bladder or rectum), maximum dose to a critical structure (e.g., bladder or rectum), and total MU); the TPS also may receive from the user an ordered sequence of optimization steps; and at block 454 the TPS then sequentially executes the optimization steps for each treatment-planning objective to optimize the multiple treatment-planning parameters and generate a treatment plan. Alternatively, the TPS may retrieve a script from memory that has a predefined ordered sequence of optimization steps, and the user provides the remainder of the treatment-planning parameters. Examples of other types of radiation treatment-planning parameters are described herein and these are used by way of example and not limitation. The optimization steps may include, for example, optimize minimum dose (OMI), optimize dose coverage (OCO), optimize homogeneity (OHI), optimize maximum dose (OMA), optimize mean dose (OME), optimize conformality (OCI), and optimize monitor units (OMU). Alternatively, other optimization steps could be implemented.

As described above, the TPS executes a first optimization step to optimize a first treatment-planning parameter, e.g., values for the minimum dose to the target volume (OMI). In this embodiment, the result of an optimization step (e.g., the minimum dose to the PTV) serves as an additional constraint (described more fully below) to subsequent optimization steps (e.g., optimizing the mean dose to the rectum) such that subsequent optimization steps cannot degrade previously optimized treatment-planning parameters (e.g., minimum dose to the PTV). Alternatively, in the prostate for example, optimizing the maximum dose to the bladder cannot degrade the previously optimized minimization of the mean dose to the rectum. Although, as more fully described below, optimized parameters may be allowed to degrade by up to a given amount specified by a relaxation value to aid the TPS in arriving at an acceptable optimization for subsequent steps.

For example, and without limitation, the optimization process may be bounded by optimization constraints, such as, maximum MU per treatment plan, maximum MU per node, maximum MU per beam, maximum doses for one or more target structures, maximum doses for one or more critical structures, and maximum doses for one or more derived structures (e.g., PTV). In one embodiment, the optimization constraints are the constraints of a multi-constraint cost function. In another embodiment, the optimization constraints are the optimized parameters of one or more optimization steps to achieve one or more treatment-planning objectives (e.g., OMI, OCO, OHI, OMA, OME, OCI, OMU, or the like). In order to optimize the optimizable parameters, other user-inputs may be used, such as, for example, goal values (e.g., VOI maximum dose and MU limits) for the optimization steps, shell dilations (i.e., of derived structures); relaxation values; convergence criteria, etc. The goal value is a user-defined or TPS-defined desired optimized value resulting from the optimization of the optimizable parameter. If the TPS achieves the goal value that optimization step is complete. However, the best the TPS can achieve is an optimum value for that particular parameter, which can be different than the goal value, but may be the same. Hence, the TPS may complete the optimization step on reaching the goal value, or on reaching the optimum value, i.e., closest possible to the goal value, if the goal value cannot be achieved. The relaxation value is the amount by which the TPS may degrade a previously optimized treatment-planning parameter in subsequent optimization steps. The relaxation value may come from user-input, or from a previously saved script. The relaxation value facilitates the TPS in achieving the goal values of or otherwise completing subsequent optimization steps. Unlike conventional methods that optimize all objectives simultaneously and collectively, embodiments of the present invention allow the TPS to individually optimize the treatment-planning objectives in sequence, and in some embodiments, relax the optimization from a previous optimization step by no more than a defined relaxation value to allow for better optimizations of subsequent optimization steps. Without relaxation of prior steps, goals for subsequent steps may not be achieved or significantly improved.

Not all parameters of the radiation treatment plan can be optimized, but may still be considered necessary for the creation of the treatment plan. For example, and without limitation, non-optimizable parameters of a treatment plan include CT image, target VOIs, VOI parameters, critical structures (also referred to as organs at risk (OARs)), set of nodes, density model parameters, or isocurve parameters. Also, other user-inputs may be used for the creation of the treatment plan, such as, for example, and without limitation, goal values, relaxation values, convergence criteria, absolute constraints, shell structure dilations for one or more of the optimization steps.

The TPS can also use user-defined or TPS-defined convergence criteria to facilitate completing an optimization step. If the TPS has difficulty reaching the goal value, for any number of different reasons appreciated by the skilled artisan, it can use the convergence criterion to say 'it is good enough', for example when the parameter being optimized does not change by a defined amount (convergence criterion) over a certain amount of time or number of iterations. For example, the TPS may specify a convergence criterion that indicates that the optimization step is complete when the current value of the optimization step changes by less than one part in ten thousand for a specified number of successive iterations without reaching the specified goal value or producing the truly optimal output for a particular treatment-planning parameters, e.g., minimum dose to the target. In effect, the convergence criteria may affect how fast the optimization step reaches an optimized value by reducing the number of iterations and/or the amount of time to reach a particular goal value. Other examples of convergence criteria will be apparent to the skilled artisan. In one embodiment, if the TPS terminates the execution of an optimization step based on the convergence criteria (meaning that neither the goal value nor an optimum value had yet been reached), the goal value for that parameter would still remain the same for subsequent optimization steps and remain subject to variance by only the relaxation value, or alternatively the goal value could be changed to the value actually achieved. In one embodiment, the convergence criteria may be turned on or off on a per-optimization-step basis via a user interface, and may be different for each of the optimization steps, allowing the ability to change the convergence criterion for each optimization step individually. For example, a user may turn on the convergence criterion for the OHI step (for which a user might not want to spend a large amount of time for a small gain in homogeneity), but may keep the convergence criterion off for a specific organ at risk step, such as a critical structure. Unlike conventional methods that optimize all objectives simultaneously and collectively, these embodiments allow the user to change the convergence criterion for each optimization step individually. Alternatively, the convergence criteria may be set on or off and collectively set to be the same for all the optimization steps in the script.

The TPS can also receive from memory or from other user-inputs (e.g., goal values, relaxation values, convergence criteria, absolute constraints, shell structure dilations). The absolute constraints, also referred to as hard constraints, are maximal limits that cannot be violated during the sequential optimization, and may limit the solution space for the sequential optimization. The absolute constraints may be, for example and without limitation, a total maximum MU for the treatment plan (e.g., maximum MU of 95000), a maximum MU per beam (e.g., 500), a maximum MU per node (e.g., 1000), a maximum dose for one or more target VOIs (e.g., 7600 cGy), a maximum dose for one or more critical structures (e.g., max dose in bladder is 4180 cGy), a maximum dose for one or more shell structures (e.g., 3800 cGy), total maximum dose, constraints on beam geometry, and constraints on beam usage. Some of these absolute constraints are described below with respect to FIGS. 5A and 5B. The shell structures are more fully described above.

Aspects of a treatment plan may also include various optimized treatment-planning parameters regarding the radiation beams of the treatment plan from the execution of the ordered sequence of optimization steps. These may include, for example and without limitation, a number of radiation beams, a node and orientation for each beam, a MU for each beam, and a field size for each beam, or other parameters related to beam geometry or beam usage. In some embodiments, characteristics of the radiation beams may be optimized as treatment-planning parameters, for example and without limitation, the TPS may minimize the number of beams with non-zero MU, or minimize the total MU. In other embodiments, instead of minimizing the number of non-zero beams, the user may set a beam MU cutoff value, then re-run the sequential optimization from the beginning without the beams whose MU values lie below this cutoff value. The advantage of reducing the number of beams with non-zero MU is that robot traversal time, and thus total treatment time, is decreased.

In one embodiment, the TPS receives treatment-planning parameters from a user through a user interface. Non-optimizable parameters, as described previously, may include (without limitation) CT images, convergence criteria, images of other modalities, absolute constraints, VOIs, set of nodes, collimator diameters, or sampling parameters. The VOI may be, for example and without limitation, a target, such as a pathological anatomy, a critical structure, or a shell structure (as described herein). Optimizable parameters, as described previously, may include (without limitation) total MU per treatment plan, per node, per beam, minimum doses for one or more targets, and derived structures (e.g., PTV), and maximum doses for one or more targets or critical structures.

In another embodiment, the TPS receives optimizable parameters, non-optimizable parameters, and/or other user-inputs (e.g., goal values, relaxation values, convergence criteria, absolute constraints, shell structure dilations for one or more of the optimization steps, etc) from memory, such as from past treatment plans for the same patient, a different patient, or from a previously stored script. The TPS may load the stored inputs and may allow a user to modify the stored inputs. In one embodiment, the optimizable and/or non-optimizable parameters and/or the user-inputs are pre-defined by a user, or alternatively are pre-defined by a manufacturer of the TPS that performs the operations described herein. Alternatively, the parameters and user-inputs may be defined in other ways as would be appreciated by one of ordinary skill in the art, such as, for example, by a learning process based on a previous treatment plan for the same anatomical volume of interest, or from a wizard-like work flow manager (described more fully above).

After receiving (either from the user, or from memory, or a combination of both) the information necessary to define optimization steps, goal values, one or more absolute constraints, optimizable, and non-optimizable parameters, the TPS executes a first optimization step to optimize a first treatment parameter to a first goal value. For example, the first goal value may represent the highest possible minimum dose delivered to the target below or equal to the maximum dose constraint (maximizing the minimum dose to the target). The first optimization step maximizes the minimum dose delivered to the target without violating any of the one or more absolute constraints. The result of the first optimization step (also referred to as an optimized treatment-planning parameter) serves as an additional constraint for subsequent optimization steps. Next, the TPS executes a second optimization step to optimize a second treatment parameter to a second goal value without violating any of the absolute constraints or the additional constraint from the first optimization step. For example, and without limitation, the second goal value may represent the highest possible mean dose in the PTV below or equal to the maximum dose constraint (maximize homogeneity), the lowest possible volume of a critical structure (e.g., rectum, bladder, etc) receiving more than a certain percentage (e.g., 75%) of the prescription dose (optimize mean dose), or the lowest possible total MU (optimize MU). The TPS, in some embodiments, may relax the result of the first optimization step by allowing the execution of the second optimization step to change the additional constraint at most by a relaxation value during execution of the second optimization step. In embodiments where the result of the first optimization step is retained as an additional constraint, the second optimization step optimizes the second optimization constraint to a second goal value without violating any of the one or more absolute constraints and without changing the additional constraint from the first optimization step by more than the relaxation value during the execution of the second optimization step. It should be noted that, if no relaxation value is applied to the result of a previous optimization step (i.e., result is a fixed constraint), the subsequent steps may have very little room for further optimization. On the other hand, applying a reasonable relaxation value to the result of the previous optimization step (i.e., result is a flexible constraint) may facilitate the successful completion of subsequent optimization steps with only a small impact to the previously optimized treatment-planning parameter. As would be appreciated by one of ordinary skill in the art, execution of one optimization step can be made more difficult or easier depending on the constraint imposed by the previous optimization steps and/or whether the constraint is fixed or flexible. Therefore, the sequence in which the optimization steps are performed may be a key factor in determining the trade-offs between multiple treatment-planning objectives.

As described above, a script is an ordered sequence of optimization steps for sequential optimization during execution of the optimization steps, as well as for storing the optimization steps for later use. FIG. 4D illustrates one embodiment of a method of generating a script. FIG. 4D is a flow diagram of one embodiment of a method 460 of generating a script having an ordered sequence of individual optimization steps. Like the method 420, the method 460 is performed by processing logic (referred to as TPS for convenience) that may comprise hardware, software, firmware, or any combination thereof. The TPS begins with receiving input, for example from a user through a user interface or from memory, to define multiple treatment-planning parameters, and multiple optimization steps to generate an optimized treatment plan (block 462). At block 464, the TPS generates a script, having an ordered sequence of optimization steps, from one or more treatment-planning parameters received at the TPS. In one embodiment, the script can be saved in memory or to an external storage device for later retrieval (block 466). In another embodiment, the TPS executes the script to optimize each of the optimization steps sequentially in the order specified by the script.

The following description regarding FIGS. 5A-7B describes various embodiments of user interfaces of the TPS that can be used for sequential optimization. The user interfaces of FIGS. 5A-7B use exemplary values for the prostate example introduced above. As will be appreciated by one of ordinary skill in the art, sequential optimization may be applied to other targets than the prostate.

Figure 5A:
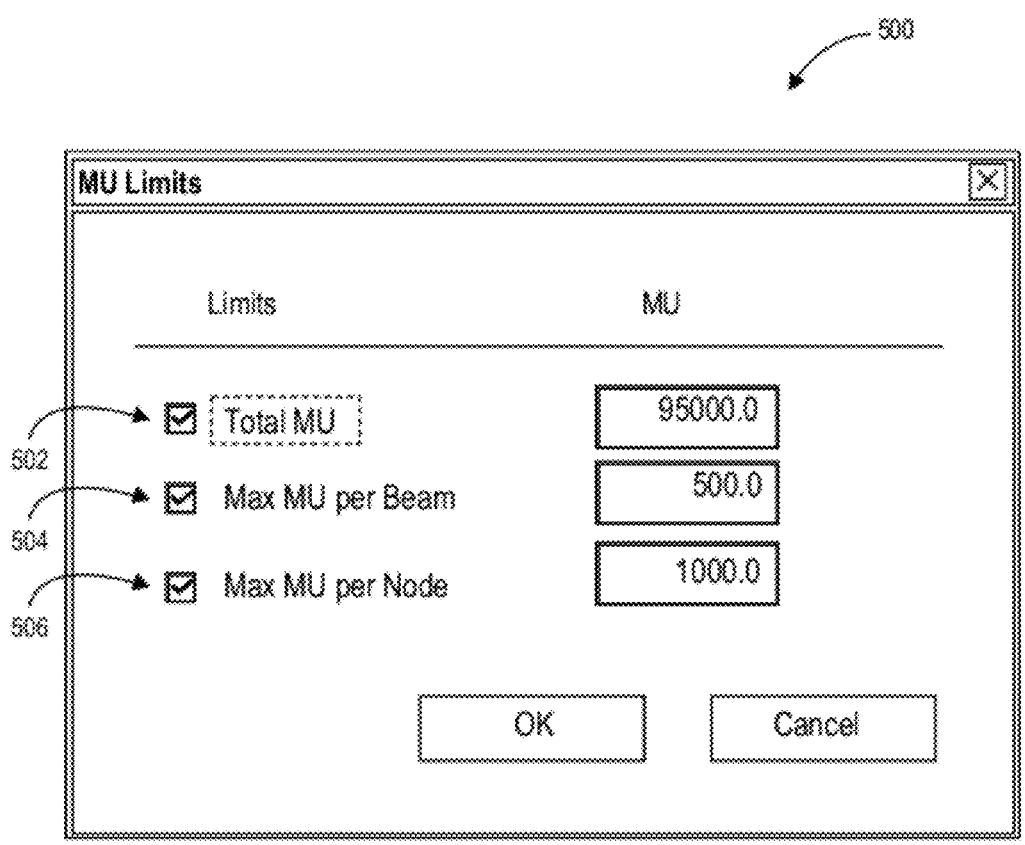
FIG. 5A illustrates one embodiment of a user interface that allows a user to define the absolute Monitor Unit (MU) constraints.

FIG. 5A illustrates one embodiment of a user interface 500 that allows a user to define absolute MU constraints, including total MU for the entire treatment plan 502, maximum MU per beam 504, and maximum MU per node 506. FIG. 5B illustrates one embodiment of a user interface 550 that allows a user to define the maximum dose for each VOI in the treatment plan (VOI limits 552), as well as sampling parameters for each VOI, voxel sampling for example. Sampling parameters, which are more fully discussed below, are parameters that can be used to specify how each VOI is to be sampled for more efficient optimization. Instead of performing the optimization process on every voxel within a VOI, it may increase optimization speed to optimize the dose at only a subset of these voxels. The TPS may use importance sampling 560 (more fully discussed below), to sample voxels for example, in which the TPS chooses only the 'most important sample points' within a specified VOI, and chooses how many sample points (e.g., 1 to 5) should be used, for example, in response to user-input. In another embodiment, instead of using importance sampling, the TPS may randomly select sample points throughout the VOI, where the user can select the overall number of points to be randomly sampled. The user interface of FIG. 5B may also allow the user to specify other optimizable and non-optimizable parameters, such as a voxel sampling skip factor 556 (e.g., between 1 and 1000), the number of voxels per beam 558 (e.g., between 1 and 5), and the number of constraints 554, as described herein. In addition, the user interface of FIG. 5B may also allow the user to select whether any particular VOI is in use 562 for the sequential optimization. Because the VOIs and radiation dose profiles for the beams are defined in terms of the three-dimensional geometry of an image (e.g., a CT image), the VOIs and radiation dose values are discretized into the voxels contained in the image. Hence, in the description that follows, when we refer to input to the optimization process (e.g. "maximum dose to each voxel"), we are describing the radiation dose value in a discrete space described by that particular image voxel.

It should be noted that FIG. 5B illustrates exemplary VOI names 564, such as the prostate, urethra, a PTV, bladder, rectum, penile bulb, and first and second PTV shell structures (as described below with respect to FIG. 5C). Alternatively, other VOIs may be used, as well as other maximum dose values 552. The user interface 550 may also specify whether the boundary voxels are to be used, for example, if the boundary only box 566 is checked.

Figure 5C:
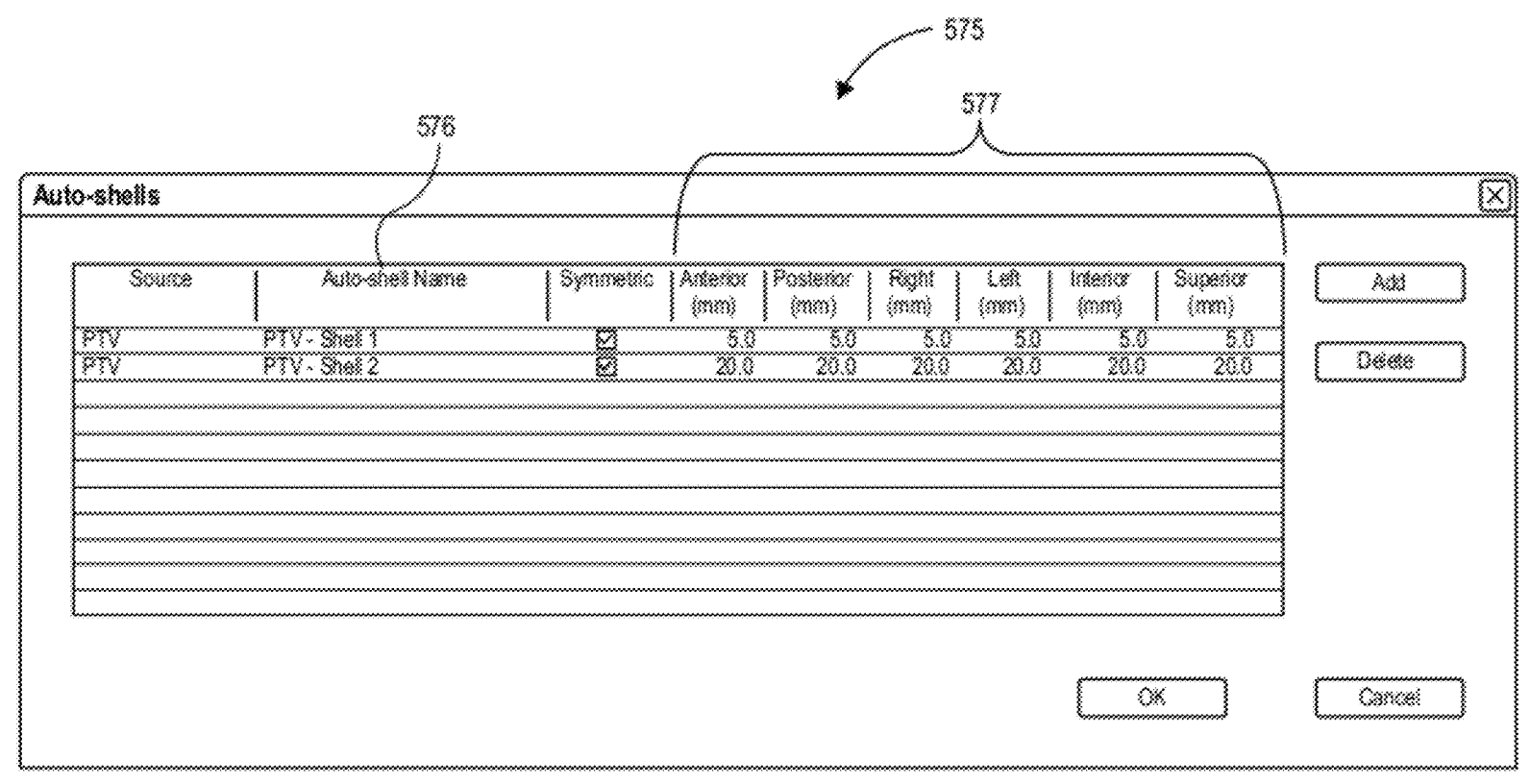

FIG. 5C illustrates one embodiment of a user interface 575 that allows a user to define the target volume for which a shell structure (e.g., PTV-Shell 1 or PTV-Shell 2) 576 is desired and the symmetric or asymmetric dilation margins 577. These shell structures 576 are tuning structures generated to restrain the dose delivered to the normal tissues surrounding the target volume, and together with maximum dose constraints may be used to control the conformality of the dose distribution around the target volume.

Figure 6:
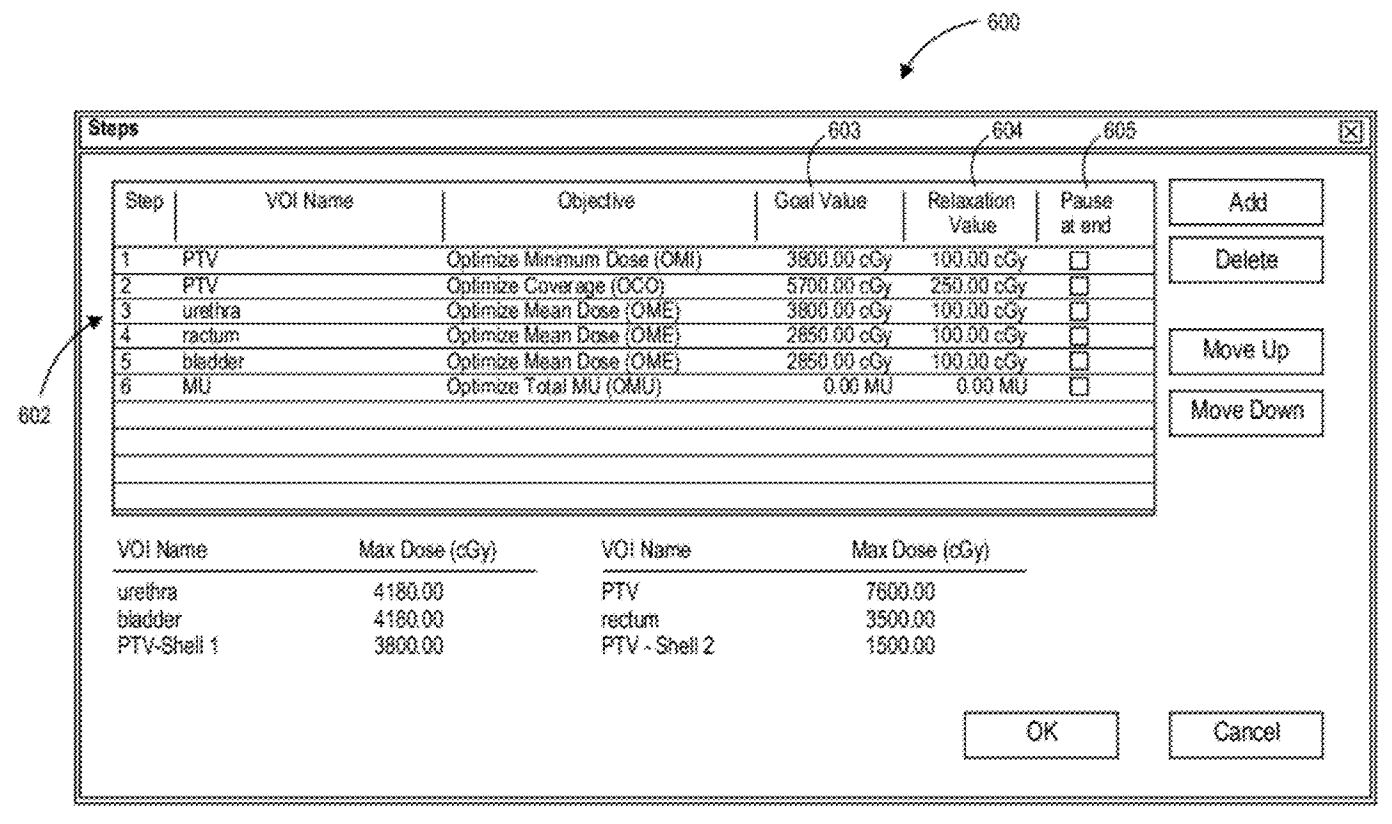

Using a sequential approach, the TPS can generate a script that sets the absolute constraints, such as those illustrated in FIGS. 5A and 5B, as well as an ordered sequence of optimization steps corresponding to a treatment-planning objective (e.g., OMI, OCO, OHI, OMA, OME, OCI, or OMU), as illustrated in FIG. 6. When executing the script, the TPS optimizes each treatment-planning objective individually, and in sequence according to the order specified by the script, such as, for example, according to an importance of the optimization steps as specified by user-input. In another embodiment, the TPS sets the order of the optimization steps according to the relative difficulty for a particular optimization step to be achieved. In another embodiment, the TPS sets the order of the script to match an order of importance of the treatment-planning objectives. Alternatively, other criteria may be used to set the order of the script, for example, the TPS may set the order according to the importance of the optimization steps and according to the relative difficulty. As described herein, the optimization steps may be applied to beam geometry properties, beam usage properties, properties of one or more VOIs, properties of the treatment plan, or the like.

FIG. 6 illustrates one embodiment of a user interface 600 that allows a user to define an ordered sequence of optimization steps 602. In the depicted embodiment of FIG. 6, the ordered sequence of optimization steps includes six steps 602, each step including a treatment-planning objective (e.g., OMI, OCO, OME, and OMU). In this embodiment, the first treatment-planning objective is to set the minimum dose to the PTV with a goal value dose 603 of reaching 3800 cGy with a relaxation value 604 of 100 cGy. The second treatment-planning objective is to maximize the volume of the PTV to having a goal value dose 603 of 5700 cGy with a relaxation value 604 of 250 cGy. Three treatment-planning objectives minimize the mean dose to the urethra, rectum, and bladder, with the goal value doses 603 of 3800, 2850, and 2850 cGy, respectively, and each with a relaxation value 604 of 100 cGy. The last treatment-planning objective is to minimize the total number of monitor units (OMU). It should also be noted that the user interface of FIG. 6 displays the maximum dose constraints for the various VOIs.

In one embodiment, the user interface 600 receives user-input from the user to define the treatment-planning objectives, the goal values 603, the relaxation values 604, and the order of the optimization steps 602. Although each of the optimization steps includes a relaxation value 604, in some embodiments, any of the relaxation values may be set to zero, such as the relaxation value 604 in the sixth optimization step. In another embodiment, the user interface 600 is automatically populated when a saved script is loaded from memory, and the user interface 600 may allow the user to edit the optimization steps of the loaded script before execution.

In the depicted embodiment, each step 602 has a pause flag 605, which, when set, causes the step 602 to pause at the end of an optimization step, and when cleared, for example, by user-input, enables the TPS to automatically begin the next optimization step after the previous optimization step is completed. In some cases, the optimization steps 602 reach their respective goal values 603 to complete the optimization step. In other cases, the optimization steps 602 reach the convergence criteria, or alternatively the optimum value, as described above.

It should be noted that similar medical conditions may use the same treatment-planning objectives in the same or similar order of relative importance or relative priority. Therefore, the script may be saved in memory and be subsequently retrieved from memory during treatment planning sessions of the same or a different patient. The TPS may store one or more scripts that may be selected by a user to use during development of the treatment plan. In one embodiment, upon selection by the user, the TPS automatically generates a script for the treatment plan. In another embodiment, the TPS may retrieve a selected script from memory in response to the user's selection, and allow the user to edit one or more optimization steps of the selected script. In one embodiment, a script includes the maximum MU constraints, the maximum dose constraints, the automatic shell structures parameters and the ordered sequence of optimization steps, as described above with respect to FIGS. 5A, 5B, and 6. Alternatively, the script may include more or less than the maximum dose constraints and the ordered sequence of optimization steps illustrated in FIGS. 5A, 5B, and 6.

Figure 7A:
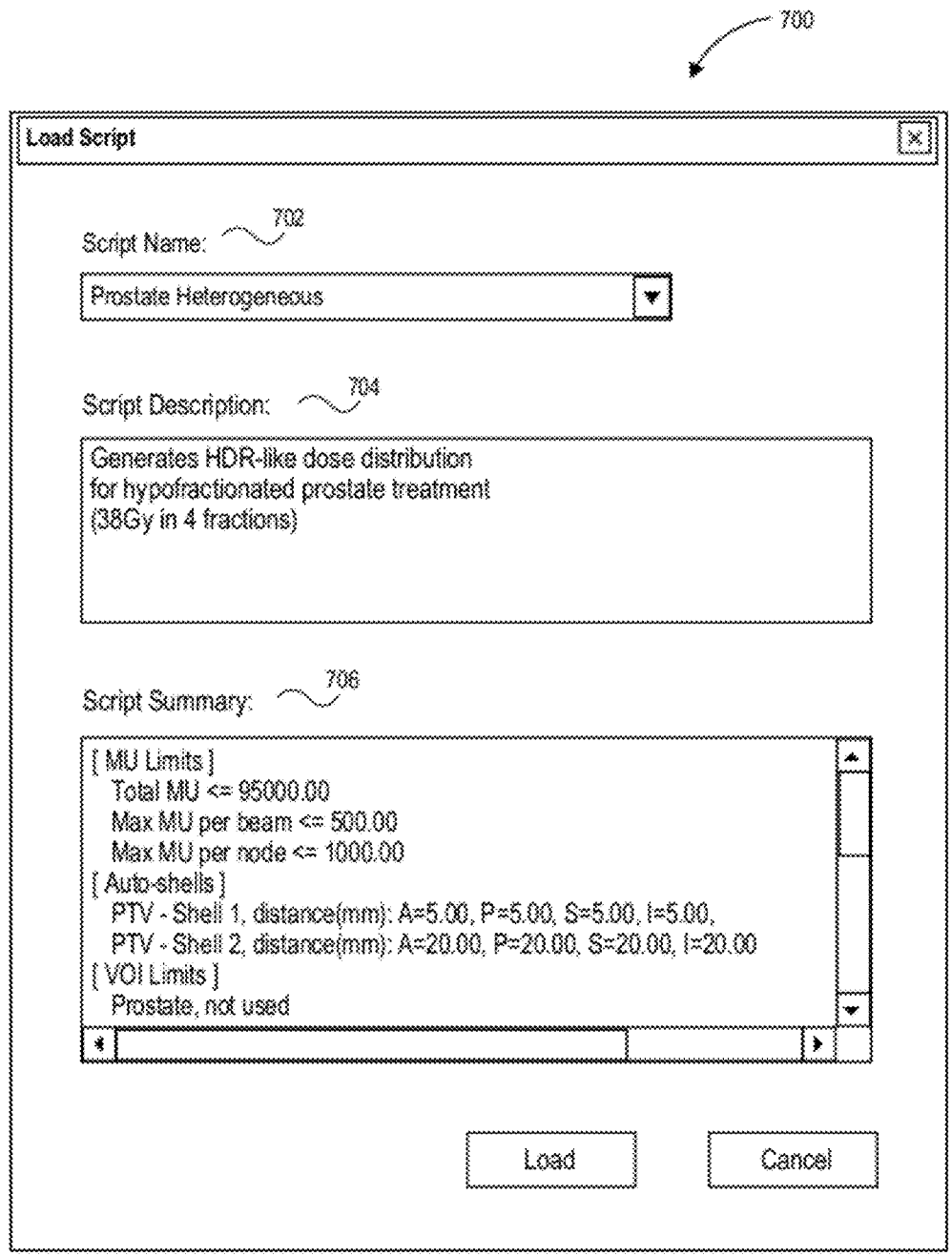
FIG. 7A illustrates one embodiment of a user interface that allows a user to load a stored script having a sequence of individual optimization steps.

FIG. 7A illustrates one embodiment of a user interface 700 that allows a user to load a stored script having a sequence of individual optimization steps. The user interface of FIG. 7A is a dialog that can load the stored script. The depicted script may be used for treatment of low-risk early-stage prostate cancer. The dialog user interface of FIG. 7A includes the script name of the stored script 702 (e.g., Prostate Heterogeneous), a script description 704, and the script summary 706, which includes the sequence of the individual optimization steps, the MU maxima constraints, and VOI maxima constraints. For example, the stored script 702 has the absolute constraints for the plan (95000 monitor units), node (1000 monitor units), and beam (500 monitor units), as described with respect to FIG. 5A. The stored script 702 also includes the maximum doses for anatomic volumes (e.g., PTV-Shell 1 and PTV-Shell 2), as described with respect to FIG. 5B. The optimization sequence of the stored script 702 is illustrated in FIG. 6. In this context, during treatment planning, after loading the CT image(s) and contouring the VOIs, the user can select the stored script 702 to be loaded. Once the stored script 702 is loaded, the user may edit one or more optimization steps associated with the stored script or add one or more additional optimization steps using the TPS. The user can use the TPS to save the modified script in memory. The user may also use TPS to match the VOIs in the treatment plan to the VOIs in the loaded script, as described with respect to FIG. 7B.

Figure 7B:
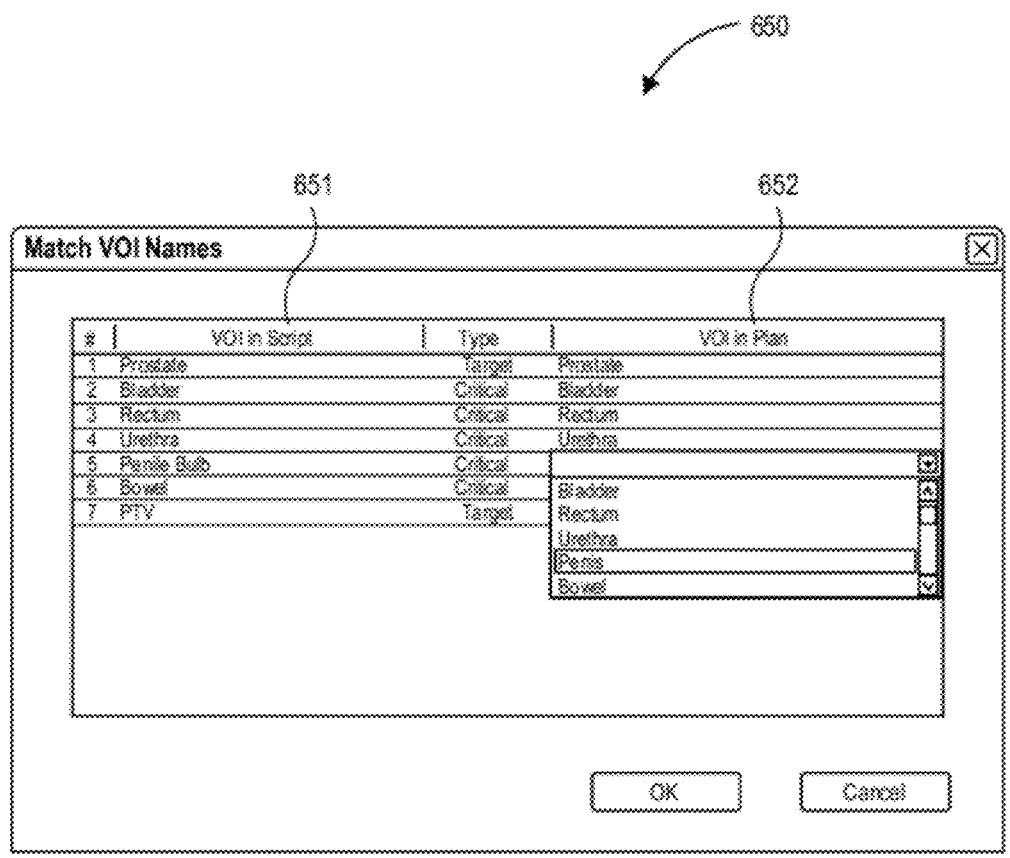
FIG. 7B illustrates one embodiment of a user interface that allows a user to match the names of the VOI in the script being loaded to the VOI names present in the treatment plan.

FIG. 7B illustrates one embodiment of a user interface 650 that allows a user to match the names of the VOI 651 in the script being loaded to the VOI names 652 in the present treatment plan. When the VOI names 651 in the script being loaded are matched to the name of the VOI 652 in the present treatment plan, the TPS can automatically load the script, and automatically execute the script or allow further modifications to the loaded script. In one embodiment, the TPS automatically matches the names of the VOI 652 in the present treatment plan to the VOI names 651 when the user selects the stored script. In another embodiment, for example, when the names do not automatically match, the user can manually match the VOI 651 in the script being loaded to the VOI 652 in the present treatment plan using the user interface 650.

Mathematical Basis for One Embodiment of Sequential Optimization

Described below is the mathematical basis for sequential optimization in accordance with embodiments of the present invention. Each optimization step of the sequential optimization process involves minimizing the linear cost function F(x), where x is a vector that contains the beam weights in MU, as expressed in equation (1):

$$F(x) = c_{maximize\_min} S^{VOI}_{maximize\_min} + \\ c_{minimize\_max} S^{VOI}_{minimize\_max} + c_{maximize\_mean} \sum_{voxels} S^{voxels}_{maximize\_mean} + \\ c_{minimize\_mean} \sum_{voxels} S^{voxels}_{minimize\_mean} + c_{minimize\_MU} \sum_{Beams} x^{beam} \quad (1)$$

The cost function minimization is performed using linear programming. The c coefficients are set to either unity or zero. The sequential nature of the algorithm is achieved by setting only one c coefficient to unity and all other coefficients to zero during the minimization procedure, thus allowing each term to be optimized individually. Therefore, the cost function is reduced to one of the five types of terms described in equation (1), and is also applied to only one VOI at a time (except for the last term, which applies to the total monitor units). It should be noted that the first four terms may be present for each VOI, so, for example, for two VOIs, there may be nine terms, of which only one has a non-zero coefficient c in any one step. The overall optimization procedure is implemented as a series of optimization steps in which the coefficients c are varied between zero and one at each optimization step. The five types of terms within the cost function are described below.

Each minimization process is constrained such that the solution cannot violate upper or lower constraints representing treatment-planning objectives. In one embodiment, only upper absolute constraints can be defined prior to the optimization. This means that the initial optimization problem is always feasible, i.e. a solution to the problem always exists, because setting all beam weights to zero gives zero radiation dose, and hence, obeys all the initial absolute constraints. Additional upper and lower constraints are added to the problem based on the results of each optimization step. Because the lower constraints can only be defined based on the results of an optimization step, the problem is guaranteed to remain feasible during the minimization process. Examples of upper and lower constraints applied during minimization are summarized in the following Table 1-1.

TABLE 1-1

Example of Constraints Applied during Minimization

| Constraint | Constraint set at start of optimization? | Constraint Can Be Updated by an Optimization Step? |
|---|---|---|
| Maximum dose within the VOI | Yes | Yes, after Optimize Maximum (OMA), Optimize Conformality (OCI), and Optimize Mean (OME) |
| Maximum dose at each voxel | Yes, but the maximum dose for each voxel is less than or equal to the VOI maximum dose constraint | Yes, after Optimize) Mean (OME may differ for each voxel |
| Minimum dose within the VOI | No | Yes, after Optimize Minimum (OMI), Optimize Coverage (OCO), or Optimize Homogeneity (OHI) |
| Minimum dose at each voxel | No | Yes, after Optimize Coverage (OCO) and Optimize Homogeneity (OHI) may differ for each voxel |
| Maximum total MU | Yes, but the default value is very large if not specified by the user | Yes, after Optimize Monitor Units (OMU) |
| Maximum MU per beam | Yes, but the default value is very large if not specified by the user | No |
| Maximum MU per node | Yes, but the default value is very large if not specified by the user | No |

The term "maximize minimal dose" ($c_{maximize\_min}^{VOI} S_{maximize\_min}^{VOI}$) of equation (1) measures the deviation of the VOI's minimum dose ($D_{min}^{VOI}$) beneath the user-defined goal value ($G_{maximize\_min}^{VOI}$). This deviation is given by equation (2):

$$S_{maximize\_min}^{VOI} \begin{cases} \leq G_{maximize\_min}^{VOI} - D_{min}^{VOI} & \text{if } D_{min}^{VOI} < G_{maximize\_min}^{VOI} \\ = 0 & \text{if } D_{min}^{VOI} \geq G_{maximize\_min}^{VOI} \end{cases} \quad (2)$$

Therefore, minimizing this term within the cost function increases the minimum dose within the VOI towards the goal value (e.g., as close as possible) without violating existing constraints (e.g., absolute constraints, or previously optimized treatment-planning parameters as modified where applicable by a relaxation value). This term is implemented as the Optimize Minimum (OMI) step and is typically available only for target VOIs.

After the OMI step, the optimal minimum dose is retained as an additional dose constraint applied to all voxels in the target VOI. As described above, the result of a previous optimization step becomes an additional constraint for a subsequent optimization step. This additional dose constraint is given by equation (3):

$$D^{voxel} = G_{maximize\_min}^{VOI} - S_{maximize\_min}^{VOI,opt} - R_{maximize\_min}^{VOI} = D_{min}^{VOI,opt} - R_{maximize\_min}^{VOI} \quad (3)$$

where $D_{min}^{VOI,opt}$ is the minimum voxel dose in the VOI after optimization, $S_{maximize\_min}^{VOI,opt}$ is the minimum deviation resulting from this optimization step, and $R_{maximize\_min}^{VOI}$ is a user-defined relaxation value. This additional dose constraint cannot be set below the VOI minimum dose defined by a previous optimization step. This guarantees that the minimal dose within the target VOI cannot decrease by more than the user-defined relaxation value as subsequent optimization steps are performed.

The term "minimize maximal dose" ($c_{minimize\_max}^{VOI}$ $S_{minimize\_max}^{VOI}$) of equation (1) measures the deviation of the VOI maximum dose ($D_{max}^{VOI}$) above the user-defined goal value ($G_{minimize\_max}^{VOI}$). This deviation is given by equation (4):

$$S_{minimize\_max}^{VOI} \quad (4)$$

$$\begin{cases} \leq D_{max}^{VOI} - G_{minimize\_max}^{VOI} & \text{if } D_{max}^{VOI} > G_{minimize\_min}^{VOI} \\ = 0 & \text{if } D_{max}^{VOI} \leq G_{minimize\_min}^{VOI} \end{cases}$$

Therefore, minimizing this term within the cost function reduces the maximum dose within the VOI to be as close as achievable to the goal value without violating the existing constraints. This term is implemented as the Optimize Maximum (OMA) optimization step when applied to a critical structure and as the Optimize Conformality (OCI) optimization step when applied to an auto-shell structure.

After this optimization step, the optimal maximum dose is retained as an additional dose constraint, applied to all voxels in the VOI. This additional constraint is given by equation (5):

$$D^{voxel} = G_{minimize\_max}^{VOI} + S_{minimize\_max}^{VOI,opt} + R_{minimize\_max}^{VOI} = D_{max}^{VOI,opt} + R_{minimize\_max}^{VOI} \quad (5)$$

where $D_{max}^{VOI,opt}$ is the maximum voxel dose in VOI after optimization, $S_{minimize\_max}^{VOI,opt}$ is the minimum deviation resulting from this optimization step, and $R_{minimize\_max}^{VOI}$ is a user-defined relaxation value. This new dose constraint cannot be set above the VOI maximum dose, defined prior to the optimization or defined by a previous optimization step. This guarantees that the maximal dose within the VOI cannot increase by more than the relaxation value as subsequent optimization steps are performed.

The term "maximize mean dose"

$$\left( c_{maximize\_mean} \sum_{voxels} S_{maximize\_mean}^{voxels} \right)$$

of equation (1) measures the summed deviation of the dose at each voxel ($D^{voxel}$) beneath the user-defined goal value ($G_{maximize\_mean}^{VOI}$). The deviation is given by equation (6):

$$S_{maximize\_mean}^{voxel} \begin{cases} \leq G_{maximize\_mean}^{VOI} - D_{min}^{voxel} & \text{if } D_{min}^{voxel} < G_{maximize\_mean}^{VOI} \\ = 0 & \text{if } D_{min}^{voxel} \geq G_{maximize\_mean}^{VOI} \end{cases} \quad (6)$$

$$\forall\ voxel \in VOI$$

Therefore, minimizing this term within the cost function increases total dose summed over all voxels (and hence the mean dose) as much as possible to be as close as achievable to the goal value without violating the existing constraints. This term is implemented as the Optimize Coverage (OCO) and Optimize Homogeneity (OHI) steps, and is available only for target VOIs. The Optimize Coverage and Optimize Homogeneity optimization steps differ only in their goals.

After this optimization step, the optimal coverage or homogeneity is retained as an additional dose constraint applied to the sum of doses from all voxels in the VOI. The additional constraint is given by equation (7):

$$S^{voxel} \begin{cases} = G_{maximize\_mean}^{VOI} - S_{maximize\_mean}^{voxel,opt} - R_{maximize\_mean}^{VOI} = S^{voxel,opt} - R_{maximize\_mean}^{VOI} \\ \quad \text{if } S^{voxel,opt} - R_{maximize\_mean}^{VOI} < G_{maximize\_mean}^{VOI} \\ = G_{maximize\_mean}^{VOI} \quad \text{if } S^{voxel,opt} - R_{maximize\_mean}^{VOI} \geq G_{maximize\_mean}^{VOI} \end{cases} \quad \forall\ voxel \in VOI \quad (7)$$

where $S_{maximize\_mean}^{VOI,opt}$ is the mean dose resulting from this optimization step, and $R_{maximize\_mean}^{VOI}$ is a user-defined relaxation value. This new constraint cannot be relaxed below the VOI minimum dose defined by a previous optimization step. In one embodiment, if the lowest dose within the VOI is larger than the previous VOI minimum dose, the new value is used. This guarantees that the minimal dose within the VOI cannot decrease by more than the relaxation value as subsequent optimization steps are performed.

The term "minimize mean dose"

$$\left( c_{minimize\_mean} \sum_{voxels} S_{minimize\_mean}^{voxels} \right)$$

of equation (1) measures the summed deviation of the dose at each voxel ($D^{voxel}$) above the user-defined goal value ($G_{minimize\_mean}^{VOI}$). The deviation is given by equation (8):

$$S_{minimize\_mean}^{voxel} \begin{cases} \leq D_{max}^{voxel} - G_{minimize\_mean}^{VOI} & \text{if } D_{max}^{voxel} > G_{minimize\_mean}^{VOI} \\ = 0 & \text{if } D_{max}^{voxel} \leq G_{minimize\_mean}^{VOI} \end{cases} \quad (8)$$

$$\forall \, voxel \in VOI$$

Therefore, minimizing this term within the cost function decreases the total dose summed over all voxels, and hence the mean dose, as much as possible to be as close as achievable to the goal value without violating the existing constraints. This term is implemented as the Optimize Mean (OME) step and is available for critical structures.

After this optimization step, the optimal mean dose is retained as an additional dose constraint applied to the summed dose over all voxels in the VOI. The new constraint is given by equation (9):

$$S^{voxel} \begin{cases} = G_{minimize\_mean}^{VOI} + S_{minimize\_mean}^{voxel,opt} + R_{minimize\_mean}^{VOI} = S^{voxel,opt} - R_{minimize\_mean}^{VOI} \\ \qquad \text{if } S^{voxel,opt} + R_{minimize\_mean}^{VOI} > G_{minimize\_mean}^{VOI} \\ = G_{minimize\_mean}^{VOI} \quad \text{if } S^{voxel,opt} + R_{minimize\_mean}^{VOI} \leq G_{minimize\_mean}^{VOI} \end{cases} \forall \, voxel \in VOI \quad (9)$$

where $S_{minimize\_mean}^{voxel,opt}$ is the mean dose resulting from this optimization step, and $R_{minimize\_mean}^{VOI}$ is a user-defined relaxation value. No voxels are constrained to dose values below the goal value. This may over-constrain the optimization problem for the subsequent optimization steps. These new constraints cannot be set above the VOI maximum dose, defined prior to the optimization or defined by a previous optimization step. In one embodiment, if the largest dose within the VOI is lower than the previous VOI maximum dose, the new value is used. This guarantees that the maximal dose within the VOI cannot increase by more than the relaxation value as subsequent optimization steps are performed.

The term "minimize monitor units"

$$\left( c_{minimize\_MU} \sum_{Beams} S_{minimize\_MU}^{beams} \right)$$

of equation (1) measures the total MUs for the treatment plan and attempts to reduce the total MUs to achieve a goal value, for example and without limitation, zero. As would be appreciated by one of ordinary skill in the art, other goal values may be used. Minimizing this term within the cost function reduces the total MU as far as possible, and therefore reduces the treatment time. This is implemented as the Optimize Monitor Units (OMU) optimization step.

After this optimization step, the optimal Monitor Units are used to update the total MU constraint given by equation 10:

$$X = \sum_{Beams} x^{beam} \leq X^{opt} + R_{minimize\_MU}^{X} \quad (10)$$

where $X^{opt}$ is the minimum value resulting from this optimization step, and $R^X$ is a user-defined relaxation value. This guarantees that the total monitor units cannot increase by more than approximately $R^X$ as subsequent optimization steps are performed.

Absolute Constraints

Initial maximum constraints are absolute throughout the optimization process. Some exemplary absolute constraints are summarized in Table 1-2.

TABLE 1-2

Absolute Constraints

| Type | Maximum | Description |
|---|---|---|
| MUs | Total MUs | Limits the total MU to minimize overall treatment time. |
| | MUs per beam | Limits the MU per beam to minimize the occurrence of high dose regions within the body or just below the skin surface that results from a single beam or from multiple beams from different nodes that pass through a single volume. |
| | MUs per node | Limits the MU per node to minimize the occurrence of high dose regions within the body that results from multiple beams from a node passing through a single volume. |

TABLE 1-2-continued

Absolute Constraints

| Type | Maximum | Description |
|---|---|---|
| Target | Maximum Dose | Limits the maximum dose delivered within a target to control dose homogeneity. If the desired uniformity of dose over the target volume is 20% between minimum and maximum doses, this constraint may be set to be about 20% larger than the prescription dose, for example. |
| Critical structure | Maximum Dose | Limits the maximum dose delivered to a critical structure to minimize the complication probability and to maximize dose conformality |
| Auto-shell structure | Maximum Dose | Limits the maximum dose delivered to an auto-shell structure to maximize dose conformality |

The initial constraints, e.g., maximum MU for each beam, for each node, and for the entire treatment plan, maximum doses for target and critical structures should not be violated during the optimization process; the constraints that are applied to ensure retention of the results of previous optimization steps during subsequent steps may be relaxed.

Optimization Steps

As described herein, in one embodiment, each optimization step of a script is designed to optimize a single treatment-planning objective to a corresponding goal value. The program attempts to achieve a result as close as possible to the goal value, but the goal value is not guaranteed.

FIG. 8 is a table of exemplary optimization steps according to one embodiment. Each entry of the table of FIG. 8 includes a type of VOI 801, a treatment-planning objective 802, a description 803, and an exemplary graph of the DVH 804. In each of the DVHs 804, line 805 represents the goal value, line 807 represents the target DVH before the optimization step, line 806 represents the target DVH after the optimization step, and the arrow(s) 808 represent the direction of the optimization step.

Constraints Established by Optimization Steps and Relaxation

As described herein, in one embodiment, the result of each optimization step is retained as an additional constraint for all subsequent optimization steps. The result of each optimization step can be retained unchanged as a new constraint or the result can be relaxed before being applied as a constraint.

Figure 9:
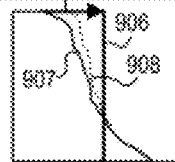
FIG. 9 is a table of exemplary objectives and how the DVH is optimized for each objective according to one embodiment.

FIG. 9 is a table of exemplary objectives and illustrates how the DVH is optimized for each objective according to one embodiment. Each entry of the table of FIG. 9 includes a type of VOI 901, a treatment-planning objective 902, a DVH of the optimization 903, a DVH of the optimization constrained without relaxation 904, and a DVH of the optimization constrained after a user-defined relaxation 905. In each of the DVHs, line 906 represents the goal value, line 907 represents the DVH at the start of the optimization step, line 908 (dotted in optimization 903 and solid in constraints without relaxation 904 and with relaxation 905) represents the DVH at the end of the optimization step, the arrow(s) 909 represent the direction of the optimization step, line 910 represents the value of the parameter being optimized at the beginning of the optimization step, and the arrow(s) 911 represent the user-defined relaxation.

For the optimization steps that apply to target volumes (e.g., OMI, OCO, and OHI), the new constraint is set to the minimum of the goal value or the (minimum) dose minus the relaxation value. Constraining the dose above the goal value may retain an undesirably high dose within the target volumes and may over-constrain the problem for the subsequent optimization steps. The new constraint is also set to be at least that minimal dose constraint established by a previous optimization step to guarantee that constraint is retained. The minimal dose constraints can only increase as more optimization steps are performed.

For the optimization steps that apply to critical structures or auto-shell structures (OMA, OME, and OCI), the new constraint is clipped to the maximum of the goal value or the (maximum) dose plus the relaxation value. Constraining the dose below the goal value may over-constrain the problem for the subsequent optimization steps. The new constraint is also clipped below the maximal dose constraint defined in the VOI limits, or established by a previous optimization step, to guarantee that maximal constraints are only decreased as more optimization steps are performed.

Ordering the Optimization Steps

As noted, mapping the order of the treatment-planning objectives into script steps is an important factor in the optimization process. Several approaches can be followed to define the sequential optimization set of absolute constraints and sequence of optimization steps depending on the treatment-planning objectives. For example, in one embodiment, if the dose to the critical structures has priority over the tumor coverage, the maximal dose constraints for the critical structures can be set at the clinical limits, then the optimization steps may be applied to optimize dose to the tumor without compromising the dose to the critical structures. In another embodiment, if tumor coverage has priority over the critical structures, the maximum dose constraints can be set to the critical structures at a reasonable value, but higher than the clinical limit value, then the tumor dose can be optimized. Next, the maximum dose can be optimized, or the mean dose to the critical structures can be optimized to reduce their maximal doses as far as possible without compromising the target volume's dose distribution. In another embodiment, if minimizing treatment time is a key objective, an absolute constraint on the total MU in the treatment plan can be set, and the total MU can be optimized during an early optimization step. However, if optimizing MU early in the sequence, the MU per beam/node constraints and/or maximum dose constraints on shell structures may be used in order to avoid the possibility of only a few beam directions being selected.

Once an appropriate set of absolute constraints and sequence of optimization steps is identified for a typical clinical application, it can be stored as a script and applied to similar clinical cases in the future. Each script may be fully editable within the user interface of the treatment planning system.

Clinical Examples

The examples below illustrate the use of sequential optimization steps in hypothetical clinical settings, including: 1) Prostate tumor cases whose main objectives are dose homogeneity and low dose to the surrounding critical structure; 2) Spine tumor cases whose main objectives are dose coverage and low dose to the spine; and 3) Lung tumor cases whose main objectives are dose conformality and limiting the treatment time. Each description is accompanied by a table that defines the optimization steps.

1) Sample Prostate Case

In this embodiment, the clinician wants to treat a prostate and deliver a dose as uniform as possible within the PTV. For example, the clinician may want at most 20% between minimum and maximum doses, and therefore, set PTV maximum to 20% larger than the prescription dose. The maximal dose to the rectum and bladder are set to the known tolerated dose for each organ. The clinician requires that the dose gradient in all directions away from the PTV be high in order to reduce the dose delivered to the normal tissue. It is known from previously-treated cases that constraining the dose close to the PTV to the prescription dose and at a further distance to 50% of the prescription dose provides good conformality without restraining the other treatment-planning objectives. Thus, two auto-shell structures are generated at these distances and the prescription dose and the 50% of the prescription dose values are set as maximum doses. The maximum total MU, MU per beam, and MU per node are set to reasonable values that were demonstrated to achieve the desired dose distribution and entry dose in similar previously-treated cases.

Several critical structures surround the prostate. Of these, the rectum has the lowest dose restriction, meaning the prescription dose should not touch the rectal wall. The goal value of the OMI step is set to the prescription dose, which will not conflict with the maximal dose to the rectal wall. It is followed by an OHI step to maximize the tumor dose homogeneity. Then, the OME steps are added to further reduce the dose to the rectum and bladder. The rectum step is performed first because the clinician gives it priority over the bladder. The goal value is set to 75% of the prescription dose in order to minimize the volume receiving more than 75% of the prescription (labeled as V75) which is known to correlate with complication probability. The OME steps are followed by an OMU step to achieve the lowest possible total MU while keeping the quality of the plan achieved from the preceding optimization steps.

TABLE 2-1

Sample Prostate Case

| Step | VOI | Step Objective | Constraints (absolute and relaxable constraints) | Step Goal Value | Step Solution (result) |
|---|---|---|---|---|---|
| 1 | PTV | Optimize Minimum Dose (OMI) | Maximum Total MU, MU per beam and MU per node. Maximum dose to PTV, Rectum, Bladder, Auto-shell 1 and Auto-shell 2. (absolute constraints) | Prescription dose | Highest possible PTV minimum dose below or equal to the prescription dose |
| 2 | PTV | Optimize Homogeneity (OHI) | Same constraints in step 1 + PTV minimum dose (result of step 1 - Relaxation) | PTV maximum dose | Largest possible volume of the PTV receiving at least the maximum dose, therefore, the maximum homogeneity. |
| 3 | Rectum | Optimize Mean Dose (OME) | Same constraints in step 2 + PTV dose homogeneity (result of step 2 - Relaxation) | 75% of the prescription dose | Lowest possible volume of the Rectum receiving more than 75% of the prescription dose, therefore, the minimum V75. |
| 4 | Bladder | Optimize Mean Dose (OME) | Same constraints in step 3 + Rectum minimum V75 (result of step 3 +Relaxation) | 75% of the prescription dose | Lowest possible volume of the Bladder receiving more than 75% of the prescription dose, therefore, the minimum V75. |
| 5 | MUs | Optimize Monitor Units (OMU) | Same constraints in step 4 + Bladder minimum V75 (result of step 4 + Relaxation) | Zero | Lowest possible total MU |

2) Sample Spine Case

In this embodiment, the clinician wants to get the best coverage to a spinal tumor while restraining the dose delivered to the spine. Dose homogeneity is not critical and the PTV maximum dose is set to a large value. The maximum dose to the spine is set to the known tolerated dose.

Constraining the 75% prescription dose line at a certain distance keeps the dose to the surrounding normal tissue low without affecting the dose to the spine or tumor coverage. An auto-shell structure is generated and 75% of the prescription dose is set as the maximum dose. The maximum total MU, MU per beam, and MU per node are set to reasonable values that were demonstrated to achieve the desired dose distribution and entry dose in similar previously-treated cases.

The tumor is located close to the spine and the dose tolerated by the spine is lower than the prescription dose. Therefore, the OMI step goal value is set to the maximum dose tolerated to the spine. It is followed by an OCO step to maximize the tumor dose coverage. Then, an OME step is added to further reduce the dose to the spine. The goal value is set to zero to minimize the mean dose to the spine. It is followed by an OMU step to get the lowest possible total MU, while keeping the quality of the treatment plan achieved by the preceding optimization step.

TABLE 2-2

Sample Spine Case

| Step | VOI | Step Objective | Constraints (absolute and relaxable constraints) | Step Goal Value | Step Solution (result) |
|---|---|---|---|---|---|
| 1 | PTV | Optimize Minimum Dose (OMI) | Maximum Total MU, MU per beam and MU per node. Maximum dose to PTV, Spine and Auto-shell 1 (absolute constraints) | Maximum dose to the spine | Highest possible PTV minimum dose below or equal to the maximum dose to the spine. |
| 2 | PTV | Optimize Coverage (OCO) | Same constraints in step 1 + PTV minimum dose (result of step 1 - Relaxation) | Prescription dose | Largest possible volume of the PTV receiving at least the prescription dose, therefore, the maximum coverage. |
| 3 | Spine | Optimize Mean Dose (OME) | Same constraints in step 2 + PTV dose coverage (result of step 2 - Relaxation) | zero | Lowest possible mean dose to the Spine. |
| 4 | MU | Optimize Monitor Units (OMU) | Same constraints in step 3 + Spine Mean Dose (result of step 3 + relaxation) | zero | Lowest possible total MU |

3) Sample Lung Case

In this embodiment, the clinician wants to treat a lesion in the left lung with a dose uniformity of about 20%. The PTV maximum dose is set to 20% larger than the prescription dose. The maximum dose to the esophagus and heart are set to the known tolerated dose for each organ.

The clinician is willing to allow a small volume of the surrounding lung tissue to receive the full prescription dose in order to achieve good coverage of the PTV, so the left lung is excluded from the optimization. However, the clinician requires a high dose gradient in all directions away from the PTV in order to reduce the average dose within the normal lung.

Previous plans of similar cases have shown that the steepest dose gradient achievable can be characterized by positioning the 75% prescription dose line and 50% prescription dose line at specific distances from the PTV. Thus, two auto-shell structures are generated at these distances and an initial maximum dose is set to the prescription dose for both auto-shell structures. The maximum total MU, MU per beam, and MU per node are set to values that have been demonstrated to achieve the desired dose distribution and entry dose in similar previously-treated cases.

No critical structure other than the lung is in close proximity to the lesion, so the OMI step goal is set to the prescription dose. The OMI step is followed by an OCO step to maximize the tumor coverage.

Then, because the principal objective in this case is to minimize treatment time, an OMU step is placed next, very early in the sequential optimization process. The OMU step is followed by two OCI steps to optimize the conformality of the dose distribution on the inner shell structure closer to the 75% prescription dose line and the outer shell structure closer to the 50% prescription dose line.

TABLE 2-3

Sample Lung Case

| Step | VOI | Step Objective | Constraints (absolute and relaxable constraints) | Step Goal Value | Step Solution (result) |
|---|---|---|---|---|---|
| 1 | PTV | Optimize Minimum Dose (OMI) | Maximum Total MU, MU per beam and MU per node. Maximum dose to PTV, heart, esophagus, Auto-shell 1 and Auto-shell 2. | Prescription dose | Highest possible PTV minimum dose below or equal to the prescription dose. |
| 2 | PTV | Optimize Coverage (OCO) | Same constraints in step 1 + PTV minimum dose (result of 1 - Relaxation) | Prescription dose | Largest possible volume of the PTV receiving at least the prescription dose, therefore, the maximum coverage. |
| 3 | MU | Optimize Monitor Units (OMU) | Same constraints in step 2 + PTV dose coverage (result of 2 - Relaxation) | zero | Lowest possible total MU. |
| 4 | Auto-shell structure 1 | Optimize Conformality (OCI) | Same constraints in step 3 + maximum total MU (result of 3 + Relaxation) | 75% of the prescription dose | Lowest possible Auto-shell structure 1 maximum dose above or equal to 75% of the prescription. |
| 5 | Auto-shell structure 2 | Optimize Conformality (OCI) | Same constraints in step 4 + Auto-shell structure 1 maximal dose (result of 4 + Relaxation) | 50% of the prescription dose | Lowest possible Auto-shell structure 2 maximum dose above or equal to 50% of the prescription. |

It should be noted that although the above embodiments describe specific values and objectives for the prostate, spine, and lung cases, in other embodiments, other values and objectives may be used.

Beam Reduction

The sequential optimization may target approximately 2,000 to 6,000 candidate beams (e.g., depending on the number of collimator sizes selected) toward the tumor(s). Typically, the sequential optimization results in a treatment plan with approximately 100-400 beams having non-zero MU. To reduce overall treatment time, beam reduction can be performed to further reduce the number of beams. Beam reduction removes from the optimization process those beams whose MU is below a user-specified cutoff, and optionally, re-optimizes using only the remaining beams. The reduction in candidate beams from thousands to hundreds results in significantly shorter optimization and treatment times. Beam reduction effectively excludes those beams that do not contribute significantly to the treatment plan and optionally re-optimizes only those beams that were found to be efficient for the current tumor volumes and critical structures. For a reasonable MU cutoff value, a treatment plan may use fewer beams, which may have fewer total MUs, and may experience negligible degradation of the dose distribution.

Generally, the re-optimization is performed using the same absolute constraints and optimization steps. However, assuming that the remaining beams are geometrically efficient for the current tumor volumes and critical structures, the same beams should also work well with slightly different optimization parameters (maximum dose limits, MU limits, goal values, and so on). Again, for a reasonable MU cutoff value, it is possible to fine tune the absolute constraints and optimization steps and take advantage of the short optimization time that results with a smaller set of candidate beams to perform a small adjustment to the dose distribution. In one embodiment, a small cutoff value can be used first to avoid compromising plan quality, and then the optimization can be re-run with an increased cutoff value if the plan quality seems to have negligible change but there are too many remaining beams at the first cutoff value. This incremental approach takes a little longer, but may avoid reducing too many beams (which cannot be restored without resetting the beamset). As would be appreciated by one of ordinary skill in the art, other configurations are possible.

Automatic Collimator Selection

In one embodiment, the sequential optimization uses an automatic collimator selection algorithm. The automatic collimator selection algorithm selects two or three fixed collimator sizes for use during the sequential optimization. This selection may be performed using a geometric heuristic based on the target volume dimensions. The user preference for homogeneity or conformality determines whether the heuristic will select larger or smaller collimator sizes respectively. In other embodiments, the automatic collimator selection algorithm can be used with a variable-sized collimator during the sequential optimization.

In practice, the conformality option is often useful when dose-limiting organs at risk are close to the target volume. In one embodiment, the TPS is designed to provide a starting point in the collimator selection process. No geometric heuristic can be guaranteed to result in the optimal planning solution (that is, the lowest overall cost term achievable with any possible combination of two or three collimator sizes). Therefore, this selection should be carefully evaluated based on a clinical understanding of the specific planning problem.

Importance Sampling

In one embodiment, the sequential optimization uses importance sampling (e.g., 560 of FIG. 5B). The treatment planning system, such as the MULTIPLAN® System, available from Accuray Incorporated of California, may sample points for optimization from the same grid as that used for dose calculation. Normally, this sampling is independent of the number or type of beams, and the number, type, and size of collimators, and the user can control the density of points by using the skip factor (e.g., 556 of FIG. 5A). For example, a skip factor of two results in approximately half the total number of sampling points for a given VOI, as compared to the complete set that results when the skip factor is set to one.

Importance sampling takes a different approach to the assignment of sampling points for optimization purposes by attempting to determine which OAR or shell structure points are likely to be the bounding maximum constraints for the OAR or shell structure. As an example, if a linear program had a set of constraints {x<5, x<7.2, x<4.5} then the constraint x<4.5 is the bounding constraint because it supersedes all of the other constraints. The basic premise of importance sampling is that the voxels in the OAR or auto-shell structure with the highest cGY per MU coefficients from a beam (e.g., beam n 1001 of FIG. 10) will be the points that are most affected by dose from the beam passing through the OAR or auto-shell structure. Only critical structures or auto-shell structures can use this method, because targets by definition require high-uniform dose and have minimum dose constraints, and all points may be part of some minimum bounding constraint.

Figure 10:
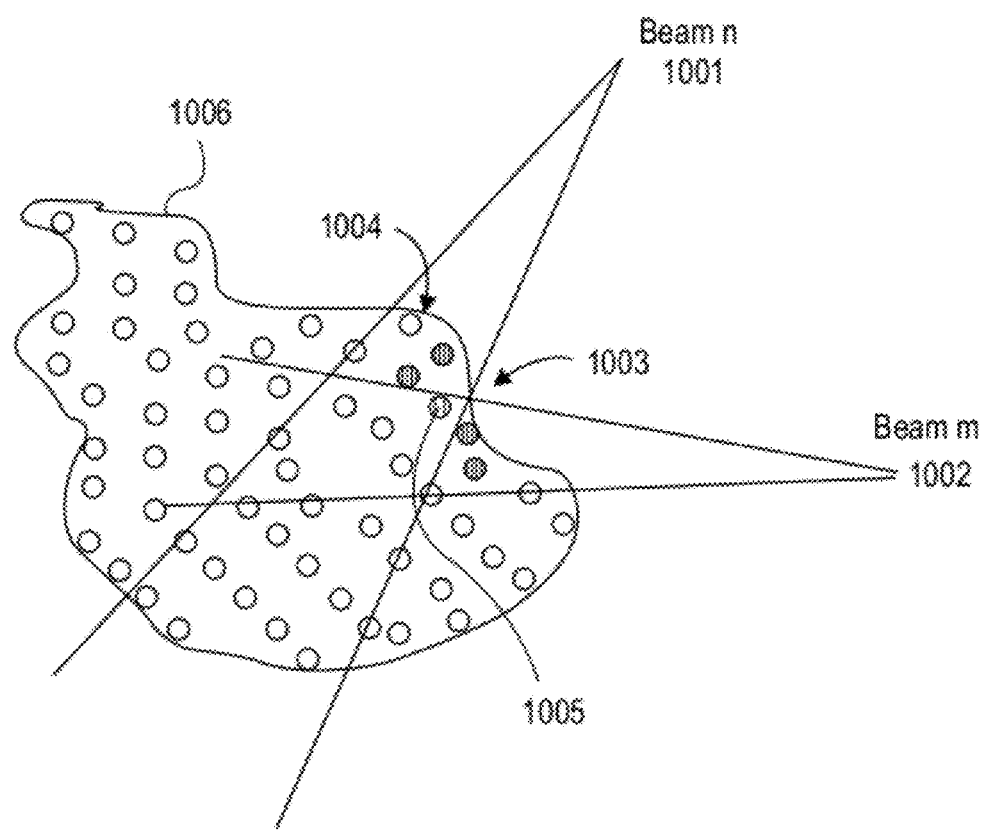
FIG. 10 illustrates one embodiment of importance sampling set to three voxels per beam.

The method of selection of the 'most important' points can be demonstrated by considering the depicted embodiment shown in FIG. 10. For a case where the importance sampling voxels per beam (e.g., 558) is set to three, the algorithm will extract the three voxels 1003 and 1004 (within the dose volume 1006) having the highest dose coefficients for each beam (e.g., beams n 1001 and m 1002). The lists of voxels 1003 and 1004 for all beams are concatenated, and any identical points (e.g., voxel 1005) that were sampled from multiple beams are removed. The importance sampling is set to three voxels per beam in FIG. 10. The beam overlap illustrated in FIG. 10 results in five voxels for the two beams. The hashed circles indicate the voxels 1003 and 1004 that are included in sampling for both illustrated beams 1001 and 1002. The total number of sampled voxels is not strictly proportional to the total number of beams. In summary, importance sampling: 1) enables entry of the number of voxels per beam (e.g., limited to 1-5); 2) is only applied to the critical structures (or their boundary voxels if the Boundary-Only box 566 is checked) and shell structures; 3) does not include the constraint points on a VOI that receives relatively little dose per MU from any beam; and 4) maintains the 'important' maximum constraints on the optimization because points receiving less dose are redundant when other points on the VOI are more tightly constrained by the same max dose bounds.

Treatment Planning System

The embodiments described herein may be implemented as a method of treatment planning, or as a treatment planning system that includes the TPS. In one embodiment, one or more portions of the TPS involves a "wizard" or "wizard-like" user interface, in which the TPS guides the user through one or more complex tasks of treatment planning. The TPS may provide a wizard or wizard-like user interface to launch the treatment planning process. For example, in one embodiment, the wizard user interface may involve step-by-step dialogs to guide the user through the treatment planning process, such as to import 3-D images, contour VOIs, to sequentially optimize the treatment plan. Specifically for sequential optimization, the wizard interface may be used to obtain user-input to define the optimization steps, the sequence of the optimization steps, one or more absolute constraints, goal values, relaxation values, or the like. In one embodiment, the wizard guides the user into the workflow for treatment planning, as described in U.S. Pat. No. 7,611,452, filed Sep. 30, 2005. As would be appreciated by one of ordinary skill in the art, other types of TPS may be used.

In one embodiment, a user can use the wizard user interface to develop a treatment plan for a particular treatment region of the patient, as described herein. In another embodiment, the user can use the wizard user interface to develop one or more scripts to be stored for later use, as described herein. In another embodiment, the user can use the wizard user interface to select a saved script in developing a current treatment plan. The saved script may provide one or more pre-defined treatment-planning parameters applicable to the anatomical treatment volume of interest. For example, in one embodiment, during treatment planning, the user may specify an anatomical region targeted for radiation treatment in the wizard user interface, such as by selecting a body region of a patient, represented in a body graphic on the user interface, for radiation treatment. Based on the selected body region, a library of suitable planning templates may be uploaded with predefined planning parameters. The treatment-planning parameters for the templates may be based on past treatments that were successful for a particular body region (e.g., cranial, spine, lung). The treatment-planning parameters may be pre-defined by the factory (e.g., the manufacturer of the TPS), pre-defined and saved by the user, or pre-defined from learning processes by the system from previous plans for the same treatment site. One such treatment-planning parameter may be a node set (or subset) best suited for optimizing treatment plan conformality, DVH, and delivery times. The user can review, modify, and accept the pre-defined planning parameter values of the saved script before beginning the optimization of the treatment plan. The user may also modify the pre-defined treatment-planning parameters and save them under a new script name for later use. The use of a wizard user interface and saved scripts, either alone or in combination, may provide an advantage of reducing the time required to complete the treatment planning process, reducing user error, and may also provide a method to simplify the various tasks involved in the treatment planning workflow.

In one embodiment, the TPS is implemented on the Windows Server 2003 product platform (alternatively, other operating system platforms may be used), and is designed to integrate with the CYBERKNIFE® system, developed by Accuray Incorporated of California, and third-party imaging systems. In one embodiment, the TPS is fully compliant with the Digital Imaging and Communications in Medicine (DICOM) standards (e.g., DICOM-RT standard) for the distribution and viewing of medical images, and the TPS is pre-configured with these utilities and requires no additional software.

In another embodiment, the TPS includes various types of algorithms for optimizing the dose distribution based on the user defined minimum/maximum dose constraints. One of these algorithms may be an iterative algorithm that optimizes deviations above the maximum dose constraint and below the minimum dose constraint. The iterative planning algorithm first generates a set of radiation beams and performs an initial dose distribution calculation, and subsequently attempts to improve the initial dose distribution calculation by altering one or more radiation beams. The other one of these algorithms may be a simplex algorithm, which involves minimizing the number of MUs subject to the minimum/maximum dose constraints. The use of either an iterative algorithm or a simplex algorithm is another treatment-planning parameter that may be preset by a script, or defined by a user. In one embodiment, a combination of both algorithms may be used. For example, the plan optimization may begin with the simplex algorithm to determine the minimal MU required, followed by the iterative algorithm, or vice versa.

In one embodiment, the treatment planning process involves aspects of both forward and inverse planning techniques, thereby combining the strengths of forward and inverse planning techniques. For example, the operator can utilize isocentric beam geometries or a mixture of non-isocentric and isocentric beam geometries as part of forward planning, and subsequently modify the topology of isodose contours directly during inverse planning. The operator can control each beam for use in the treatment plan in terms of a radiation emission point, a distance to the target region, an orientation, and a radiation dose weight. Alternatively, the characteristics of each beam may be pre-set according to the treatment-planning parameters of a selected template. The TPS can allow the operator to specify a set of radiation beams (and associated paths, emission points, and dose weights) to be used as part of a forward planning process, and another set of beams to be used as part of inverse planning. The set of beams reserved for inverse planning may be optimized by utilizing one or more envelopes of constraint points generated automatically by the treatment planning system.

Figure 11:
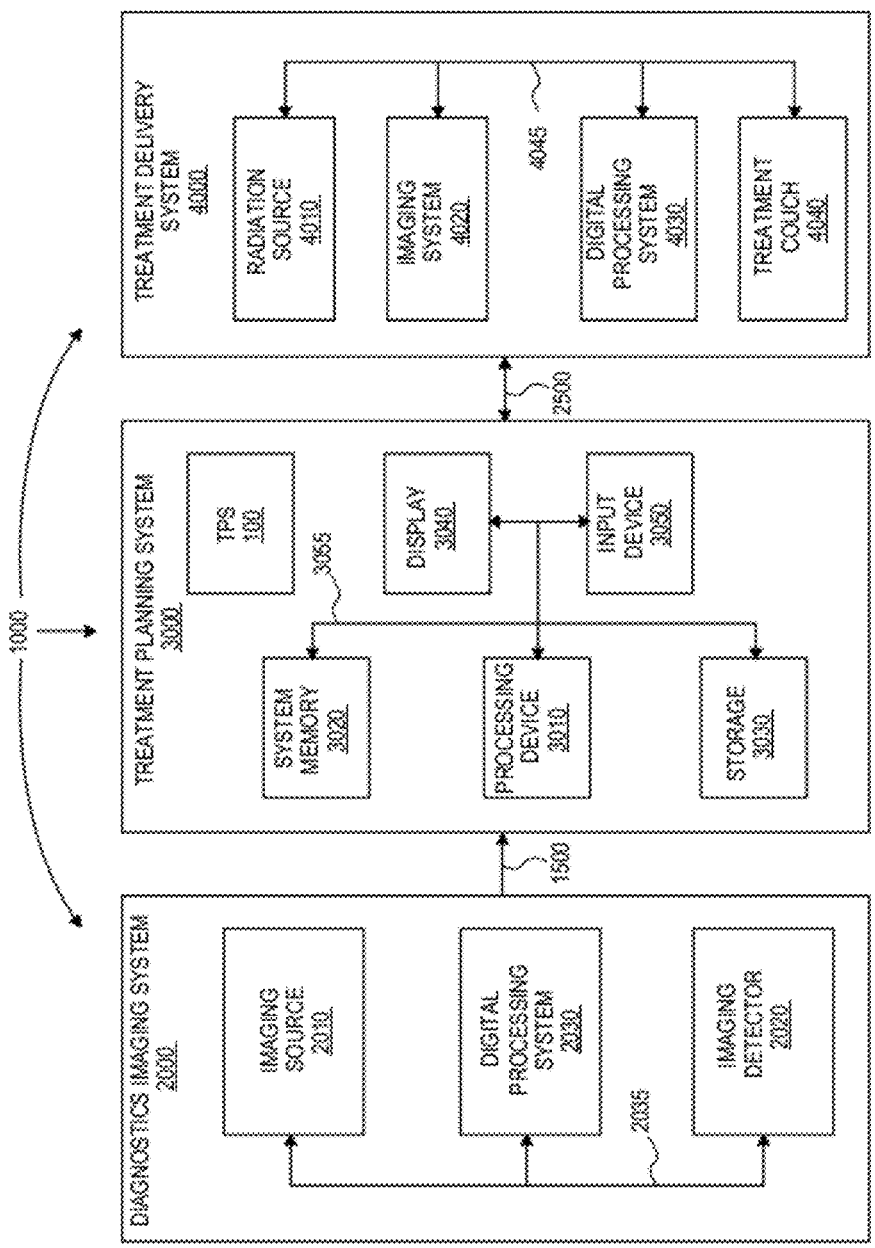
FIG. 11 illustrates one embodiment of systems that may be used to perform radiation treatment in which features of the present invention may be implemented.

FIG. 11 illustrates one embodiment of systems that may be used to perform radiation treatment in which features of the present invention may be implemented. As described below and illustrated in FIG. 11, system 1000 includes a diagnostic imaging system 2000, a treatment planning system 3000, and a treatment delivery system 4000.

Diagnostic imaging system 2000 may be any system capable of producing medical diagnostic images of a VOI in a patient that may be used for subsequent medical diagnosis, treatment planning and/or treatment delivery. For example, diagnostic imaging system 2000 may be a CT system, a magnetic resonance imaging (MRI) system, a positron emission tomography (PET) system, an ultrasound (US) system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 includes two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s), which may be diametrically opposed to the x-ray sources. A single large imaging detector, or multiple imaging detectors, may also be used that would be illuminated by each x-ray imaging source. As would be appreciated by one of ordinary skill in the art, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP), or other types of processing devices, such as a controller, field programmable gate array (FPGA), or the like. Digital processing system 2030 may also include other components (not shown) such as memory, storage devices, network adapters and the like. Digital processing system 2030 may be configured to generate digital diagnostic images in a standard format, such as the DICOM format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data. Processing device 3010 may represent one or more general-purpose processors (e.g., a microprocessor), special purpose processor such as a DSP, or other types of processing devices, such as a controller, FPGA, or the like. Processing device 3010 may be configured to execute instructions for performing the TPS operations discussed herein, for example, sequentially optimizing multiple treatment-planning parameters, generating a script for the treatment plan, guiding the user through the wizard user interface, allowing the user to select a stored script, or the like.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage devices coupled to bus 3055 for storing static information and instructions for processing device 3010. In one embodiment, the system memory 3020 is the machine-readable storage medium having stored thereon instructions, which when executed by the processing device, perform the operations described herein regarding sequential optimization.

Treatment planning system 3000 may also include storage device 3030, representing one or more storage devices (e.g., a magnetic disk drive or optical disk drive) coupled to bus 3055 for storing information and instructions. Storage device 3030 may be used for storing instructions for performing the treatment planning steps discussed herein, such as the sequential optimization algorithms.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user-input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM imports (so images can be fused and targets delineated on different systems and then imported into the treatment planning system for planning and dose calculations), expanded image fusion capabilities that allow the user to treatment plan and view dose distributions on any one of the various imaging modalities (e.g., MRI, CT, PET, etc.). Additional details of the treatment planning systems would be appreciated by one of ordinary skill in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a DSP, or other types of processing devices, such as a controller, FPGA, or the like. Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

Figure 12:
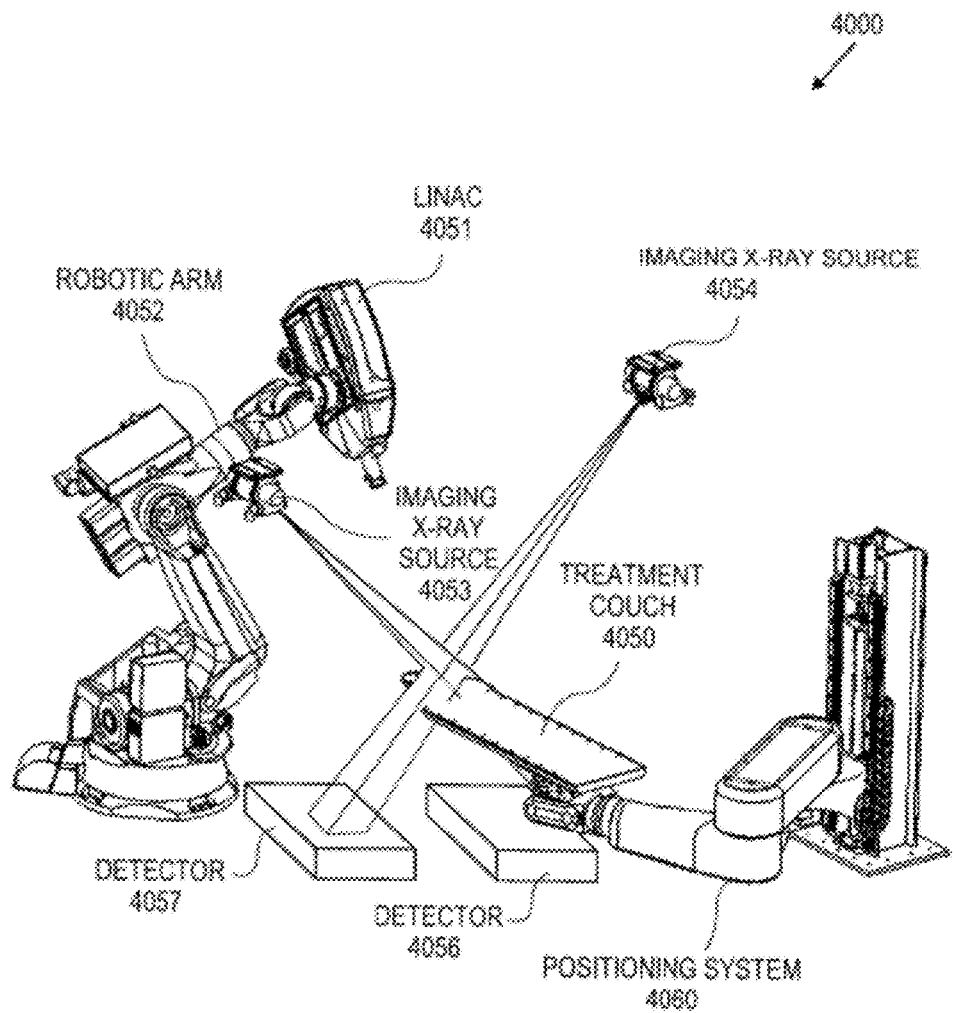
FIG. 12 illustrates another embodiment of a treatment delivery system.

In one embodiment, as illustrated in FIG. 12, treatment delivery system 4000 may be an image-guided, robotic-based radiation treatment system (e.g., for performing radiosurgery) such as the CYBERKNIFE® system, developed by Accuray Incorporated of California. In FIG. 12, the radiation source 4010 is represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered either in a single session (monofraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment-planning phase.

In FIG. 12, the imaging system 4020 is represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. As would be appreciated by one of ordinary skill in the art, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to position the radiation source with respect to the target volume.

The treatment couch 4050 may be coupled to another robotic arm of a positioning system 4060 having multiple (e.g., 5 or more) degrees of freedom, such as the ROBOCOUCH® treatment couch, developed by Accuray Incorporated. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the AXUM® treatment couch developed by Accuray Incorporated of California, or other types of treatment tables as would be appreciated by one of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met. In one particular embodiment, the gantry based system may have an O-ring with a LINAC mounted on a gimbaled head assembly.

In other embodiments, yet another type of treatment delivery system 4000 may be used, for example, a stereotactic frame system such as the GAMMAKNIFE®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry), and seismic surveying. In such applications, for example, "treatment" may refer generally to the application of radiation beam(s).

Embodiments of the present invention include various steps, as described herein. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, which may include a machine-readable storage medium having stored thereon instructions, which may be used to program a computer system (or other electronic devices) to perform a method of the operations described herein. A machine-readable medium includes any mechanism for storing or transmitting information in a form (e.g., software, processing application) readable by a machine (e.g., a computer). The machine-readable storage medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM), flash memory, or other types of medium suitable for storing electronic instructions. The machine-readable transmission medium may include, but is not limited to, electrical, optical, acoustical, or other type of medium suitable for transmitting electronic instructions.

Embodiments of the present invention may also be practiced in distributed computing environments where the machine-readable storage medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

In the foregoing specification, the invention has been described with reference to specific exemplary embodiments thereof. It will be evident, however, that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A computer-implemented method, comprising:
receiving at a treatment planning system a plurality of radiation treatment-planning parameters, wherein the plurality of radiation-treatment planning parameters represent characteristics of radiation applied to an anatomical region via radiation beams; and
sequentially optimizing the plurality of radiation treatment-planning parameters using the treatment planning system to obtain an optimized treatment plan of a plurality of radiation beams to be directed at the anatomical region, wherein sequentially optimizing comprises sequentially and individually optimizing the plurality of treatment-planning parameters in an order specified by a script, and wherein the script is a sequence of optimization steps.

2. A non-transitory computer-readable storage medium having instructions stored thereon that, when executed by a processing device of a treatment planning system, cause the treatment planning system to perform operations, comprising:
receiving at the treatment planning system a plurality of radiation treatment-planning parameters, wherein the plurality of radiation-treatment planning parameters represent characteristics of radiation applied to an anatomical region via radiation beams; and
sequentially optimizing, by the processing device of the treatment planning system, the plurality of radiation treatment-planning parameters to obtain an optimized treatment plan of a plurality of radiation beams to be directed at the anatomical region, wherein sequentially optimizing comprises sequentially and individually optimizing the plurality of treatment-planning parameters in an order specified by a script, and wherein the script is a sequence of optimization steps.

3. A treatment planning system, comprising:
a processing device to receive a plurality of radiation treatment-planning parameters, wherein the plurality of radiation-treatment planning parameters represent characteristics of radiation applied to an anatomical region via radiation beams, wherein in sequentially optimizing, and wherein the processing device is configured to sequentially and individually optimize the plurality of treatment-planning parameters in an order specified by a script, and wherein the script is a sequence of optimization steps.

4. The treatment planning system of claim 3, wherein the plurality of treatment-planning parameters comprises a plurality of optimization constraints of an optimization cost function, and wherein in sequentially and individually optimizing, the processing device is configured to:
execute a first optimization step of the script to optimize a first optimization constraint of the plurality of optimization constraints to a first goal value;
apply a result of the first optimization step as an additional constraint for subsequent optimization steps; and
execute one or more subsequent optimization steps of the script to optimize one or more additional optimization constraints of the plurality of optimization constraints without violating the additional constraint.

5. The treatment planning system of claim 4, wherein in sequentially and individually optimizing, the processing device is further configured to relax the result of the first optimization step at most by a relaxation value during execution of the one or more subsequent optimization steps.

6. The treatment planning system of claim 4, wherein in sequentially and individually optimizing, the processing device is further configured to sequentially optimize each of the optimization steps without violating any of one or more absolute constraints.

7. The treatment planning system of claim 4, wherein the first optimization step is applied to a target volume of interest (VOI), and wherein at least one of the one or more subsequent optimization steps is applied to a critical structure.

8. The treatment planning system of claim 3, further comprising a memory coupled with the processing device, the memory to store the script.

9. The treatment planning system of claim 3, wherein each of the plurality of optimization steps of the script corresponds with a treatment-planning objective, and wherein in sequentially and individually optimizing, the processing device is further configured to:
   define a first of the plurality of optimization steps to be applied to a planned target volume (PTV) containing at least a portion of the prostate of a patient, wherein the first optimization step comprises optimizing a minimum dose (OMI) to the PTV to achieve a first treatment-planning objective;
   define a second of the plurality of optimization steps to be applied to the PTV, wherein the second optimization step comprises optimizing homogeneity (OHI) of the PTV to achieve a second treatment-planning objective;
   define a third of the plurality of optimization steps to be applied to a first volume of interest (VOI) containing at least a portion of the rectum, wherein the third optimization step comprises optimizing a mean dose (OME) of the first VOI to achieve a third treatment-planning objective;
   define a fourth of the plurality of optimization steps to be applied to a second VOI containing at least a portion of the bladder, wherein the fourth optimization step comprises optimizing a mean dose (OME) of the second VOI to achieve a fourth treatment-planning objective; and
   sequentially execute the first, second, third, and fourth optimization steps individually and in sequence.

10. The treatment planning system of claim 3, wherein the processing device is further configured to define one or more absolute constraints that cannot be violated during said sequentially optimizing, wherein the one or more absolute constraints comprise at least one of the following:
   a maximum monitor units (MU) for the treatment plan;
   a maximum MU per beam; and
   a maximum MU per node.

11. The treatment planning system of claim 3, wherein in sequentially and individually optimizing, the processing device is further configured to:
   define a maximum dose for a first shell structure that at least partially surrounds a planned target volume (PTV) containing at least a portion of a target volume in the anatomical region; and
   define a maximum dose for a second shell structure that at least partially surrounds the PTV, wherein the maximum dose for the first shell structure is less than the maximum dose for the second shell structure.

12. The treatment planning system of claim 3, wherein each of the plurality of optimization steps of the script corresponds with a treatment-planning objective, and wherein in sequentially and individually optimizing, the processing device is further configured to:
   define a first of the plurality of optimization steps to be applied to a planned target volume (PTV) near the spine of a patient, wherein the first optimization step comprises optimizing a minimum dose (OMI) to the PTV to achieve a first treatment-planning objective;
   define a second optimization step to be applied to the PTV, wherein the second optimization step comprises optimizing coverage (OCO) of the PTV to achieve a second treatment-planning objective;
   define a third optimization step to be applied to a first volume of interest (VOI) containing at least a portion of the spine, wherein the third optimization step comprises optimizing a mean dose (OME) of the first VOI to achieve a third treatment-planning objective;
   define a fourth optimization step to optimize a total of monitor units (MU) in the treatment plan to achieve a fourth treatment-planning objective; and
   sequentially optimize the first, second, third, and fourth optimization steps individually and in sequence.

13. The treatment planning system of claim 3, wherein each of the plurality of optimization steps of the script corresponds with a treatment-planning objective, and wherein in sequentially and individually optimizing, the processing device is further configured to:
   define a first optimization step to be applied to a planned target volume (PTV) near a lung of a patient, wherein the first optimization step comprises optimizing a minimum dose (OMI) to the PTV to achieve a first treatment-planning objective;
   define a second optimization step to be applied to the PTV, wherein the second optimization step comprises optimizing coverage (OCO) of the PTV to achieve a second treatment-planning objective;
   define a third optimization step to optimize a total of monitor units (MU) in the treatment plan to achieve a third treatment-planning objective;
   define a fourth optimization step to be applied to a first shell structure that at least partially surrounds the PTV, wherein the fourth optimization step comprises optimizing conformality (OCI) of the first shell structure to achieve a fourth treatment-planning objective;
   define a fifth optimization step to be applied to a second shell structure that at least partially surrounds the PTV, wherein the fifth optimization step comprises optimizing conformality (OCI) of the second shell structure to achieve a fifth treatment-planning objective, wherein the maximum dose for the first shell structure is less than the maximum dose for the second shell structure; and
   sequentially optimize the first, second, third, fourth, and fifth optimization steps individually and in sequence.

* * * * *